(12) United States Patent
Tachibana et al.

(10) Patent No.: US 12,171,407 B2
(45) Date of Patent: Dec. 24, 2024

(54) ATHERECTOMY CATHETER DRIVE ASSEMBLIES

(71) Applicant: Avinger, Inc., Redwood, CA (US)

(72) Inventors: Brian Y. Tachibana, Oakland, CA (US); Charles W. McNall, Cottonwood Heights, UT (US); Michael Zung, San Carlos, CA (US); Peter Howard Smith, Pacifica, CA (US); Brian Chiu, San Francisco, CA (US); Douglas Joseph Scott Bourne, Campbell, CA (US); Priyanshu Gupta, Hornsby (AU)

(73) Assignee: Avinger, Inc., Redwood City, CA (US)

( * ) Notice: Subject to any disclaimer, the term of this patent is extended or adjusted under 35 U.S.C. 154(b) by 109 days.

(21) Appl. No.: 17/645,722

(22) Filed: Dec. 22, 2021

(65) Prior Publication Data

US 2022/0183545 A1    Jun. 16, 2022

Related U.S. Application Data

(63) Continuation of application No. 16/372,112, filed on Apr. 1, 2019, now Pat. No. 11,206,975, which is a
(Continued)

(51) Int. Cl.
*A61B 1/00* (2006.01)
*A61B 1/04* (2006.01)
(Continued)

(52) U.S. Cl.
CPC ............ *A61B 1/04* (2013.01); *A61B 1/00066* (2013.01); *A61B 1/00126* (2013.01);
(Continued)

(58) Field of Classification Search
CPC ............ A61B 1/00066; A61B 1/00126; A61B 1/00133; A61B 1/0016; A61B 1/00165;
(Continued)

(56) References Cited

U.S. PATENT DOCUMENTS

| 3,367,727 A | 2/1968 | Ward et al. |
| 3,908,637 A | 9/1975 | Doroshow |

(Continued)

FOREIGN PATENT DOCUMENTS

| CN | 1875242 A | 12/2006 |
| CN | 1947652 A | 4/2007 |

(Continued)

OTHER PUBLICATIONS

Rosenthal et al.; U.S. Appl. No. 18/337,852 entitled "Atherectomy catheter with laterally-displaceable tip," filed Jun. 20, 2023.
(Continued)

*Primary Examiner* — Mark D Remaly
(74) *Attorney, Agent, or Firm* — Shay Glenn LLP

(57) ABSTRACT

A drive assembly for driving an imaging catheter has a rotatable fiber and a rotatable drive shaft. The drive assembly includes a fiber optic rotating junction and a motor configured to rotate the rotatable portion of the fiber optic rotating junction. In some embodiments, the drive assembly includes a sensor configured to detect a rotational position of the fiber optic rotating junction and a processor configured to obtain the detected rotational position and stop the motor only when the fiber optic rotating junction is in a predetermined rotational position. In some embodiments, the motor includes a hollow shaft through which at least a portion of the fiber optic rotating junction extends.

10 Claims, 27 Drawing Sheets

Related U.S. Application Data continuation of application No. 15/162,391, filed on May 23, 2016, now Pat. No. 10,244,934, which is a continuation of application No. 14/400,151, filed as application No. PCT/US2013/032089 on Mar. 15, 2013, now Pat. No. 9,345,398.

(60) Provisional application No. 61/697,743, filed on Sep. 6, 2012, provisional application No. 61/646,843, filed on May 14, 2012.

(51) Int. Cl.
*A61B 1/07* (2006.01)
*A61B 1/313* (2006.01)
*A61B 5/00* (2006.01)
*A61B 17/3207* (2006.01)

(52) U.S. Cl.
CPC ........ *A61B 1/00133* (2013.01); *A61B 1/0016* (2013.01); *A61B 1/00165* (2013.01); *A61B 1/07* (2013.01); *A61B 1/3137* (2013.01); *A61B 5/0066* (2013.01); *A61B 17/320758* (2013.01)

(58) Field of Classification Search
CPC ........... A61B 1/04; A61B 1/07; A61B 1/3137; A61B 17/320758; A61B 5/0066
See application file for complete search history.

(56) References Cited

U.S. PATENT DOCUMENTS

| | | |
|---|---|---|
| 4,178,935 A | 12/1979 | Gekhaman et al. |
| 4,487,206 A | 12/1984 | Aagard |
| 4,527,553 A | 7/1985 | Upsher |
| 4,552,554 A | 11/1985 | Gould et al. |
| 4,578,061 A | 3/1986 | Lemelson |
| 4,598,710 A | 7/1986 | Kleinberg et al. |
| 4,611,600 A | 9/1986 | Cohen |
| 4,621,353 A | 11/1986 | Hazel et al. |
| 4,639,091 A | 1/1987 | Huignard et al. |
| 4,651,753 A | 3/1987 | Lifton |
| 4,654,024 A | 3/1987 | Crittenden et al. |
| 4,681,106 A | 7/1987 | Kensey et al. |
| 4,686,982 A | 8/1987 | Nash |
| 4,691,708 A | 9/1987 | Kane |
| 4,729,763 A | 3/1988 | Henrie |
| 4,771,774 A | 9/1988 | Simpson et al. |
| 4,781,186 A | 11/1988 | Simpson et al. |
| 4,808,163 A | 2/1989 | Laub |
| 4,841,977 A | 6/1989 | Griffith et al. |
| 4,842,578 A | 6/1989 | Johnson et al. |
| 4,850,354 A | 7/1989 | McGurk-Burleson et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,002,560 A | 3/1991 | Machold et al. |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,217,479 A | 6/1993 | Shuler |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,372,601 A | 12/1994 | Lary |
| 5,383,460 A | 1/1995 | Jang et al. |
| 5,383,467 A | 1/1995 | Auer et al. |
| 5,425,273 A | 6/1995 | Chevalier |
| 5,425,371 A | 6/1995 | Mischenko |
| 5,429,136 A | 7/1995 | Milo et al. |
| 5,431,673 A | 7/1995 | Summers et al. |
| 5,437,284 A | 8/1995 | Trimble |
| 5,449,372 A | 9/1995 | Schmaltz et al. |
| 5,459,570 A | 10/1995 | Swanson et al. |
| 5,460,168 A | 10/1995 | Masubuchi et al. |
| 5,465,147 A | 11/1995 | Swanson |
| 5,507,725 A | 4/1996 | Savage et al. |
| 5,507,760 A | 4/1996 | Wynne et al. |
| 5,507,795 A | 4/1996 | Chiang et al. |
| 5,517,998 A | 5/1996 | Madison |
| 5,529,580 A | 6/1996 | Kusunoki et al. |
| 5,556,405 A | 9/1996 | Lary |
| 5,607,394 A | 3/1997 | Andersen et al. |
| 5,613,981 A | 3/1997 | Boyle et al. |
| 5,620,426 A | 4/1997 | Braithwaite |
| 5,632,754 A | 5/1997 | Farley et al. |
| 5,632,755 A | 5/1997 | Nordgren et al. |
| 5,667,490 A | 9/1997 | Keith et al. |
| 5,674,232 A | 10/1997 | Halliburton |
| 5,676,012 A | 10/1997 | Ceriale |
| 5,681,336 A | 10/1997 | Clement et al. |
| 5,690,634 A | 11/1997 | Muller et al. |
| 5,722,403 A | 3/1998 | McGee et al. |
| 5,728,148 A | 3/1998 | Bostrom et al. |
| 5,749,846 A | 5/1998 | Edwards et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,851,212 A | 12/1998 | Zirps et al. |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,935,139 A | 8/1999 | Bates |
| 5,938,602 A | 8/1999 | Lloyd |
| 5,938,671 A | 8/1999 | Katoh et al. |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Domhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,217,549 B1 | 4/2001 | Selmon et al. |
| 6,228,076 B1 | 5/2001 | Winston et al. |
| 6,241,744 B1 | 6/2001 | Imran et al. |
| 6,283,957 B1 | 9/2001 | Hashimoto et al. |

(56) References Cited

U.S. PATENT DOCUMENTS

| | | |
|---|---|---|
| 6,285,903 B1 | 9/2001 | Rosenthal et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,375,615 B1 | 4/2002 | Flaherty et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,009 B1 | 9/2002 | Dasilva et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Teamey et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |
| 6,579,298 B1 | 6/2003 | Bruneau et al. |
| 6,599,296 B1 | 7/2003 | Gillick et al. |
| 6,615,071 B1 | 9/2003 | Casscells, III et al. |
| 6,629,953 B1 | 10/2003 | Boyd |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,673,042 B1 | 1/2004 | Samson et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Teamney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,776,062 B2 | 8/2010 | Bessellink et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,002,763 B2 | 8/2011 | Berthiaume et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 | 4/2014 | Patel et al. |
| 8,911,459 B2 | 12/2014 | Simpson et al. |
| 9,119,662 B2 | 9/2015 | Moberg |
| 9,125,562 B2 | 9/2015 | Spencer et al. |
| 9,333,007 B2 | 5/2016 | Escudero et al. |
| 9,345,398 B2 | 5/2016 | Tachibana et al. |
| 9,345,406 B2 | 5/2016 | Spencer et al. |
| 9,345,510 B2 | 5/2016 | Patel et al. |
| 9,345,511 B2 | 5/2016 | Smith et al. |
| 9,351,757 B2 | 5/2016 | Kusleika |
| 9,498,247 B2 | 11/2016 | Patel et al. |
| 9,498,600 B2 | 11/2016 | Rosenthal et al. |
| 9,557,156 B2 | 1/2017 | Kankaria |
| 9,572,492 B2 | 2/2017 | Simpson et al. |
| 9,579,157 B2 | 2/2017 | Moberg |
| 9,592,075 B2 | 3/2017 | Simpson et al. |
| 9,642,646 B2 | 5/2017 | Patel et al. |
| 9,788,790 B2 | 10/2017 | Black et al. |
| 9,854,979 B2 | 1/2018 | Smith et al. |
| 9,918,734 B2 | 3/2018 | Patel et al. |
| 9,949,754 B2 | 4/2018 | Newhauser et al. |
| 10,052,125 B2 | 8/2018 | Rosenthal et al. |
| 10,130,386 B2 | 11/2018 | Simpson et al. |
| 10,244,934 B2 | 4/2019 | Tachibana et al. |
| 10,335,173 B2 | 7/2019 | Carver et al. |
| 10,342,491 B2 | 7/2019 | Black et al. |
| 10,349,974 B2 | 7/2019 | Patel et al. |
| 10,357,277 B2 | 7/2019 | Patel et al. |
| 10,363,062 B2 | 7/2019 | Spencer et al. |
| 10,406,316 B2 | 9/2019 | Garvey et al. |

(56) References Cited

U.S. PATENT DOCUMENTS

| | | |
|---|---|---|
| 10,470,795 B2 | 11/2019 | Patel et al. |
| 10,548,478 B2 | 2/2020 | Simpson et al. |
| 10,568,520 B2 | 2/2020 | Patel et al. |
| 10,568,655 B2 | 2/2020 | Simpson et al. |
| 10,722,121 B2 | 7/2020 | Smith et al. |
| 10,729,326 B2 | 8/2020 | Spencer et al. |
| 10,806,484 B2 | 10/2020 | Simpson et al. |
| 10,860,484 B2 | 10/2020 | Simpson et al. |
| 10,869,685 B2 | 12/2020 | Patel et al. |
| 10,932,670 B2 | 3/2021 | Smith et al. |
| 10,952,615 B2 | 3/2021 | Kankaria |
| 10,952,763 B2 | 3/2021 | Newhauser et al. |
| 11,033,190 B2 | 6/2021 | Patel et al. |
| 11,076,773 B2 | 8/2021 | Patel et al. |
| 11,096,717 B2 | 8/2021 | Gupta et al. |
| 11,134,849 B2 | 10/2021 | Simpson et al. |
| 11,135,019 B2 | 10/2021 | Spencer et al. |
| 11,147,583 B2 | 10/2021 | Patel et al. |
| 11,206,975 B2 | 12/2021 | Tachibana et al. |
| 11,224,459 B2 | 1/2022 | Patel et al. |
| 11,278,248 B2 | 3/2022 | Christensen |
| 11,284,839 B2 | 3/2022 | Black et al. |
| 11,284,916 B2 | 3/2022 | Patel et al. |
| 2001/0005788 A1 | 6/2001 | McGuckin, Jr. |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082585 A1 | 6/2002 | Carroll et al. |
| 2002/0082626 A1 | 6/2002 | Donohoe et al. |
| 2002/0097400 A1 | 7/2002 | Jung et al. |
| 2002/0111548 A1 | 8/2002 | Swanson et al. |
| 2002/0115931 A1 | 8/2002 | Strauss et al. |
| 2002/0138091 A1 | 9/2002 | Pflueger |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0114875 A1 | 6/2003 | Sjostrom |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0163085 A1* | 8/2003 | Tanner ............... A61M 25/0136 604/95.01 |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0193140 A1 | 9/2004 | Griffin et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0021075 A1 | 1/2005 | Bonnette et al. |
| 2005/0027199 A1 | 2/2005 | Clarke |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0149096 A1 | 7/2005 | Hilal et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 | 8/2005 | Maschke |
| 2005/0192496 A1 | 9/2005 | Maschke |
| 2005/0197623 A1 | 9/2005 | Leeflang et al. |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0050019 A1 | 3/2007 | Hyde |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0167710 A1 | 7/2007 | Unal et al. |
| 2007/0196926 A1 | 8/2007 | Soito et al. |
| 2007/0213618 A1 | 9/2007 | Li et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bel et al. |
| 2008/0015618 A1 | 1/2008 | Sonnenschein et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |

(56) References Cited

U.S. PATENT DOCUMENTS

| | | |
|---|---|---|
| 2008/0065125 A1 | 3/2008 | Olson |
| 2008/0065205 A1 | 3/2008 | Nguyen et al. |
| 2008/0095421 A1 | 4/2008 | Sun et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0132929 A1 | 6/2008 | O'Sullivan et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0154296 A1 | 6/2008 | Taylor et al. |
| 2008/0177138 A1 | 7/2008 | Courtney et al. |
| 2008/0186501 A1 | 8/2008 | Xie |
| 2008/0207996 A1 | 8/2008 | Tsai |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2008/0287795 A1 | 11/2008 | Klingensmith et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0043191 A1 | 2/2009 | Castella et al. |
| 2009/0073444 A1 | 3/2009 | Wang |
| 2009/0073455 A1 | 3/2009 | Onimura |
| 2009/0076447 A1 | 3/2009 | Casas et al. |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196477 A1 | 8/2009 | Cense |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0234220 A1 | 9/2009 | Maschke |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0268159 A1 | 10/2009 | Xu et al. |
| 2009/0275966 A1 | 11/2009 | Mitusina |
| 2009/0284749 A1 | 11/2009 | Johnson et al. |
| 2009/0292199 A1 | 11/2009 | Bielewicz et al. |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0004544 A1 | 1/2010 | Toida |
| 2010/0021926 A1 | 1/2010 | Noordin |
| 2010/0049225 A1 | 2/2010 | To et al. |
| 2010/0080016 A1 | 4/2010 | Fukui et al. |
| 2010/0082000 A1 | 4/2010 | Honeck et al. |
| 2010/0125253 A1 | 5/2010 | Olson |
| 2010/0130996 A1 | 5/2010 | Doud et al. |
| 2010/0198081 A1 | 8/2010 | Hanlin et al. |
| 2010/0217245 A1 | 8/2010 | Prescott |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0312263 A1 | 12/2010 | Moberg et al. |
| 2010/0317973 A1 | 12/2010 | Nita |
| 2010/0324472 A1 | 12/2010 | Wulfman |
| 2011/0023617 A1 | 2/2011 | Yu et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0137140 A1 | 6/2011 | Teamney et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0123352 A1 | 5/2012 | Fruland et al. |
| 2012/0136350 A1 | 5/2012 | Goshgarian et al. |
| 2012/0203230 A1 | 8/2012 | Adams |
| 2012/0238869 A1 | 9/2012 | Schmitt et al. |
| 2012/0259337 A1 | 10/2012 | del Rio et al. |
| 2012/0277730 A1 | 11/2012 | Salahieh et al. |
| 2012/0289971 A1 | 11/2012 | Segermark et al. |
| 2013/0023865 A1 | 1/2013 | Steinke et al. |
| 2013/0035692 A1 | 2/2013 | Sorensen et al. |
| 2013/0072787 A1 | 3/2013 | Wallace et al. |
| 2013/0184549 A1 | 7/2013 | Avitall et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0287282 A1 | 10/2013 | Yokota et al. |
| 2013/0317519 A1 | 11/2013 | Romo et al. |
| 2013/0325003 A1 | 12/2013 | Kapur et al. |
| 2013/0331819 A1 | 12/2013 | Rosenman et al. |
| 2014/0005534 A1 | 1/2014 | He et al. |
| 2014/0046250 A1 | 2/2014 | Jain et al. |
| 2014/0128893 A1 | 5/2014 | Guggenheimer et al. |
| 2014/0187949 A1 | 7/2014 | Zhao et al. |
| 2014/0222042 A1 | 8/2014 | Kessler et al. |
| 2014/0222047 A1 | 8/2014 | Vreeman |
| 2014/0275996 A1 | 9/2014 | Stigall |
| 2014/0371718 A1 | 12/2014 | Alvarez et al. |
| 2015/0025310 A1 | 1/2015 | Everingham et al. |
| 2015/0141816 A1 | 5/2015 | Gupta et al. |
| 2015/0320975 A1 | 11/2015 | Simpson et al. |
| 2016/0144155 A1 | 5/2016 | Simpson et al. |
| 2018/0207417 A1 | 7/2018 | Zung et al. |
| 2019/0029714 A1 | 1/2019 | Patel et al. |
| 2019/0110809 A1 | 4/2019 | Rosenthal et al. |
| 2019/0313941 A1 | 10/2019 | Radjabi |
| 2020/0060718 A1 | 2/2020 | Patel et al. |
| 2020/0323553 A1 | 10/2020 | Fernandez et al. |
| 2021/0059713 A1 | 3/2021 | Patel et al. |
| 2021/0076949 A1 | 3/2021 | Smith et al. |
| 2021/0177262 A1 | 6/2021 | Spencer et al. |
| 2021/0267621 A1 | 9/2021 | Simpson et al. |
| 2021/0330345 A1 | 10/2021 | Newhauser et al. |
| 2021/0345903 A1 | 11/2021 | Patel et al. |
| 2022/0007941 A1 | 1/2022 | Kankaria |
| 2022/0031168 A1 | 2/2022 | Patel et al. |
| 2022/0039658 A1 | 2/2022 | Smith et al. |
| 2022/0039828 A1 | 2/2022 | Patel et al. |
| 2022/0071656 A1 | 3/2022 | Patel et al. |
| 2022/0168011 A1 | 6/2022 | Patel et al. |
| 2022/0273336 A1 | 9/2022 | Fernandez et al. |
| 2022/0273337 A1 | 9/2022 | Patel et al. |
| 2023/0225616 A1 | 7/2023 | Patel et al. |
| 2024/0057942 A1 | 2/2024 | Black et al. |

(56) References Cited

U.S. PATENT DOCUMENTS

| | | |
|---|---|---|
| 2024/0122479 A1 | 4/2024 | Smith et al. |
| 2024/0148253 A1 | 5/2024 | Simpson et al. |
| 2024/0180584 A1 | 6/2024 | Patel et al. |

FOREIGN PATENT DOCUMENTS

| | | |
|---|---|---|
| CN | 101601581 A | 12/2009 |
| CN | 103027727 A | 4/2013 |
| CN | 104968285 A | 10/2015 |
| DE | 202006018883.5 U | 2/2007 |
| EP | 0347098 A2 | 12/1989 |
| EP | 0808638 A1 | 11/1997 |
| EP | 0845692 B1 | 11/2005 |
| EP | 1859732 A1 | 11/2007 |
| EP | 2090245 A1 | 8/2009 |
| EP | 2353526 B1 | 9/2013 |
| JP | S62-275425 A | 11/1987 |
| JP | 03502060 A | 2/1990 |
| JP | H05501065 A | 3/1993 |
| JP | 05103763 A | 4/1993 |
| JP | 06027343 A | 2/1994 |
| JP | H07184888 A | 7/1995 |
| JP | 07308393 A | 11/1995 |
| JP | 2002214127 A | 7/2002 |
| JP | 2004509695 A | 4/2004 |
| JP | 2004516073 A | 6/2004 |
| JP | 2005114473 A | 4/2005 |
| JP | 2005230550 A | 9/2005 |
| JP | 2005249704 A | 9/2005 |
| JP | 2005533533 A | 11/2005 |
| JP | 2008175698 A | 7/2006 |
| JP | 2006288775 A | 10/2006 |
| JP | 2006313158 A | 11/2006 |
| JP | 2006526790 A | 11/2006 |
| JP | 2006326157 A | 12/2006 |
| JP | 200783053 A | 4/2007 |
| JP | 200783057 A | 4/2007 |
| JP | 2007225349 A | 9/2007 |
| JP | 2007533361 A | 11/2007 |
| JP | 2008023627 | 2/2008 |
| JP | 2008128708 A | 6/2008 |
| JP | 2008145376 A | 6/2008 |
| JP | 2008183208 A | 8/2008 |
| JP | 2008253492 A | 10/2008 |
| JP | 200914751 A | 1/2009 |
| JP | 2009509690 A | 3/2009 |
| JP | 200978150 A | 4/2009 |
| JP | 2009066252 A | 4/2009 |
| JP | 2009201969 A | 9/2009 |
| JP | 2010042182 A | 2/2010 |
| JP | 2010518900 A | 6/2010 |
| JP | 2011517601 A | 6/2011 |
| JP | 2011521747 A | 7/2011 |
| JP | 2012143558 A | 8/2012 |
| JP | 2012229976 A | 11/2012 |
| JP | 2012533353 A | 12/2012 |
| JP | 2013512736 A | 4/2013 |
| JP | 2013/524930 A | 6/2013 |
| JP | 2015533584 A | 11/2015 |
| JP | 2016508758 A | 3/2016 |
| KR | 2007/0047221 A | 5/2007 |
| RU | 218585902 | 7/2002 |
| RU | 2218191 C2 | 12/2003 |
| WO | WO91/17698 A1 | 11/1991 |
| WO | WO99/23958 A1 | 5/1999 |
| WO | WO00/54659 A1 | 9/2000 |
| WO | WO01/15609 A1 | 3/2001 |
| WO | WO01/76680 A1 | 10/2001 |
| WO | WO2006/133030 A2 | 12/2006 |
| WO | WO2008/005888 A2 | 1/2008 |
| WO | WO2008/029506 A1 | 3/2008 |
| WO | WO2008/042987 A2 | 4/2008 |
| WO | WO2008/051951 A1 | 5/2008 |
| WO | WO2008/065600 A2 | 6/2008 |
| WO | WO2008/086613 A1 | 7/2008 |
| WO | WO2008/087613 A2 | 7/2008 |
| WO | WO2008/151155 A2 | 12/2008 |
| WO | WO2009/005779 A1 | 1/2009 |
| WO | WO2009/006335 A1 | 1/2009 |
| WO | WO2009/009799 A1 | 1/2009 |
| WO | WO2009/009802 A1 | 1/2009 |
| WO | VO2009/023635 A1 | 2/2009 |
| WO | WO2009/024344 A1 | 2/2009 |
| WO | WO2009/094341 A2 | 7/2009 |
| WO | WO2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO2012/057940 A1 | 5/2012 |
| WO | WO2012/061935 A1 | 5/2012 |
| WO | WO2012/123737 A1 | 9/2012 |
| WO | WO2012/166332 A1 | 12/2012 |
| WO | WO2013/033490 A1 | 3/2013 |
| WO | WO2013/056262 A1 | 4/2013 |
| WO | WO2014/077870 A1 | 5/2014 |
| WO | WO2014/093148 A2 | 6/2014 |

OTHER PUBLICATIONS

Patel et al.; U.S. Appl. No. 18/550,243 entitled "Occlusion-crossing devices," filed Sep. 12, 2023.

Patel; U.S. Appl. No. 18/480,452 entitled "Occlusion-crossing devices," filed Oct. 3, 2023.

Aziz et al.; Chronic total occlusions—a stiff challenge requiring a major breakthrough: is there light at the end of the tunnel?; Heart; vol. 91; suppl. III; pp. 42-48; Jun. 2005.

Bayer Material Science: : Snap-Fit Joints for Plastics; 26 pages; retrieved from the Internet: (https://web.archive.org/web/20121119232733if_/http://fab.cba.mit.edu:80/classes/S62.12/people/vernelle.noel/Plastic_ Snap_fit_design.pdf) on Sep. 26, 2018.

Choma et al.; Sensitivity advantage of swept source and fourier domain optical coherence tomography; Optics Express; 11(18); pp. 2183-2189; Sep. 8, 2003.

De Boer et al.; Improved signal-to-noise ratio in spectral-domain compared with time-domain optical coherence tomography; Optics Letters; 28(21); pp. 2067-2069; Nov. 2003.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Han et al.; In situ Frog Retina Imaging Using Common-Path OCT with a Gold-Coated Bare Fiber Probe; CFM6; San Jose, California; CLEO, May 4, 2008; 2 pages.

Leitgeb et al.; Performance of fourier domain vs time domain optical coherence tomography; Optics Express; 11(8); pp. 889-894; Apr. 21, 2003.

Linares et al.; Arbitrary single-mode coupling by tapered and nontapered grin fiber lenses; Applied Optics; vol. 29; No. 28; pp. 4003-4007; Oct. 1, 1990.

Merriam Webster; Proximal (Definition); 10 pages; retrieved from the internet (https://www.merriam-webster.com/dictionary/proximal) on Jun. 9, 2021.

Muller et al.; Time-gated infrared fourier-domain optical coherence tomography; CFM5; San Jose, California; CLEO May 4, 2008; 2 pages.

Rollins et al.; Optimal interferometer designs for optical coherence tomography; Optics Letters; 24(21); pp. 1484-1486; Nov. 1999.

Schmitt et al.; A new rotational thrombectomy catheter: System design and first clinical experiences; Cardiovascular and Interventional Radiology; Springer-Verlag; 22(6); pp. 504-509; Nov. 1, 1999.

Sharma et al.; Common-path optical coherence tomography with side-viewing bare fiber probe for endoscopic optical coherence tomography; Rev. Sci. Instrum.; vol. 78; 113102; 5 pages: Nov. 6, 2007.

(56) References Cited

OTHER PUBLICATIONS

Sharma et al.; Optical coherence tomography based on an all-fiber autocorrelator using probe-end reflection as reference; CWJ13; San Francisco, California; CLEO May 16, 2004; 4 pages.

Shinkle et al.; Evaluation of stent placement and outcomes with optical coherence tomography; Interv. Cardiol.; 2(4); pp. 535-543; (manuscript version, 12 pages); Aug. 2010.

Stamper et al.; Plaque characterization with optical coherence tomography. Journal of the American College of Cardiology. 47(8); pp. 69-79; Apr. 18, 2006.

Suparno et al.; Light scattering with single-mode fiber collimators; Applied Optics; vol. 33; No. 30; pp. 7200-7205; Oct. 20, 1994.

Tanaka et al.; Challenges on the frontier of intracoronary imaging: atherosclerotic plaque macrophage measurement by optical coherence tomography; Journal of Biomedical Optics; 15(1); pp.(011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Wikipedia; Hinge; 4 pages; retrieved from the internet (https://en.wikipedia.org/w/index.php?title=Hinge&oldid=479569345) on Jun. 9, 2021.

Gupta et al.; U.S. Appl. No. 17/445,648 entitled "Tissue collection device for catheter," filed Aug. 23, 2021.

Simpson et al.; U.S. Appl. No. 17/449,867 entitled "Occlusion-crossing devices, imaging, and atherectomy devices," filed Oct. 4, 2021.

Spencer et al.; U.S. Appl. No. 17/449,895 entitled "Occlusion-crossing devices, atherectomy devices, and imaging," filed Oct. 4, 2021.

Patel et al.; U.S. Appl. No. 17/816,673 entitled "Atherectomy catheter with serrated cutter," filed Aug. 1, 2022.

Black et al.; U.S. Appl. No. 17/652,073 entitled "Optical coherence tomography for biological imaging," filed Feb. 22, 2022.

Patel et al.; U.S. Appl. No. 17/762,815 entitled "Atherectomy catheter with shapeable distal tip," filed Mar. 23, 2022.

Patel et al.; U.S. Appl. No. 17/763,810 entitled "Occlusion-crossing devices," filed Mar. 25, 2022.

Simpson et al.; U.S. Appl. No. 18/582,526 entitled "Identification of elastic lamina to guide interventional therapy," filed Feb. 20, 2024.

Patel.; U.S. Appl. No. 18/716,831 entitled "Atherectomy catheter with shapeable distal tip," filed Jun. 5, 2024.

\* cited by examiner

ATHERECTOMY CATHETER DRIVE ASSEMBLIES

CROSS REFERENCE TO RELATED APPLICATIONS

This application is a continuation of U.S. patent application Ser. No. 16/372,112, filed on Apr. 1, 2019, titled "ATHERECTOMY CATHETER DRIVE ASSEMBLIES," now U.S. Pat. No. 11,206,975, which is a continuation of U.S. patent application Ser. No. 15/162,391, filed on May 23, 2016, titled "ATHERECTOMY CATHETER DRIVE ASSEMBLIES," now U.S. Pat. No. 10,244,934, which is a continuation of U.S. patent application Ser. No. 14/400,151, filed on Nov. 10, 2014, titled "ATHERECTOMY CATHETER DRIVE ASSEMBLIES," now U.S. Pat. No. 9,345,398, which is a 371 of International Patent Application No. PCT/US2013/032089, filed on Mar. 15, 2013, titled "ATHERECTOMY CATHETER DRIVE ASSEMBLIES," now International Publication No. WO 2013/172974, which claims priority to U.S. Provisional Patent Application No. 61/646,843, filed on May 14, 2012, titled "ATHERECTOMY CATHETERS WITH IMAGING," and U.S. Provisional Patent Application No. 61/697,743, filed on Sep. 6, 2012, titled "BALLOON ATHERECTOMY CATHETERS WITH IMAGING," each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

A significant body of scientific and clinical evidence supports atherectomy as a viable primary or adjunctive therapy prior to stenting for the treatment of occlusive arterial disease. Atherectomy offers a simple mechanical advantage over alternative therapies. By removing the majority of plaque mass (debulking), a larger initial lumen is created. As a result, stent deployment is greatly enhanced. Moreover, there are advantages to atherectomy related to the arterial healing response. When circumferential radial forces are applied to the vasculature, as in the case of angioplasty or stenting, the plaque mass is displaced, forcing the vessel wall to stretch dramatically. This stretch induces injury which is a known stimulus for the cellular in-growth that leads to restenosis. By removing the disease with minimal force applied to the vessel and reducing the plaque burden prior to stent placement, large gains in lumen size can be created with decreased vessel wall injury and limited elastic recoiling. These effects have been shown to generate better acute results and lower restenosis rates.

Traditional atherectomy devices have been plagued by a number of problems that have severely limited market adoption of these devices. A significant concern in adopting these devices is that they tend to require the use of large, cumbersome, and expensive drive assemblies to control the rotation and/or axial translation of the atherectomy cutter. The drive assemblies described herein may overcome some of these hurdles.

SUMMARY OF THE DISCLOSURE

Described herein are drive assemblies for catheters having a rotatable cutter and on-board imaging.

In general, in one embodiment, a drive assembly for driving an imaging catheter has a rotatable fiber and a rotatable drive shaft. The drive assembly includes a fiber optic rotating junction having a stationary portion with a stationary fiber therein and a rotatable portion with a rotatable fiber therein. The drive assembly includes a first optical connection configured to connect the stationary fiber with a light source. The drive assembly includes a motor configured to rotate the rotatable portion of the fiber optic rotating junction. The drive assembly includes a second optical connection configured to connect the rotatable portion of the fiber optic rotating junction with both the drive shaft and the rotatable fiber of the imaging catheter so as to transmit torque from the motor to the drive shaft and the rotatable fiber of the catheter and so as to transmit light from the light source to the rotatable fiber of the catheter. The drive assembly includes a sensor configured to detect a rotational position of the fiber optic rotating junction. The drive assembly includes a processor configured to obtain the detected rotational position and stop the motor only when the fiber optic rotating junction is in a predetermined rotational position.

This and other embodiments can include one or more of the following features. The sensor can be a slot sensor configured to detect a flat on the rotary optical junction. The drive assembly can further include a locking mechanism configured to lock a handle of the imaging catheter to the drive assembly. The locking mechanism can include mechanical features to physically align the handle with respect to the drive assembly. The locking mechanism can be configured such that physical alignment of the catheter handle with respect to the drive assembly can further align an optical connection of the handle with the predetermined rotational position of the fiber optic rotating junction. The stationary and rotatable fibers can be configured to transmit an optical coherence tomography signal.

In general, in one embodiment, a method of driving an imaging catheter having a rotatable fiber and a rotatable drive shaft includes connecting a stationary fiber of a stationary portion of a fiber optic rotating junction in a drive assembly with a light source; connecting a rotatable fiber of the fiber optic rotating junction with the drive shaft and the rotatable fiber of the imaging catheter; rotating the rotatable portion of a fiber optic rotating junction with a motor in the drive assembly such that both the drive shaft and the rotatable fiber of the imaging catheter rotate and such that light is transmitted from the light source to the rotatable fiber of the imaging catheter; sensing a position of the fiber optic rotating junction; and stopping the motor based upon the sensed position only when the fiber optic rotating junction is in a predetermined rotational position.

This and other embodiments can include one or more of the following features. Sensing the position can include sensing the position with a slot sensor. The method can include locking a handle of the imaging catheter into the drive assembly. The locking mechanism can include mechanical features to physically align the catheter handle with respect to the drive assembly. Locking the handle of the imaging catheter into the drive assembly using the mechanical features can align an optical connection of the handle with the predetermined rotational position of the fiber optic rotating junction. The method can further include transmitting an optical coherence tomography signal through the stationary and rotatable fibers.

In general, in one embodiment, a drive assembly for driving an imaging catheter having a rotatable fiber and a rotatable drive shaft includes a drive assembly housing. The drive assembly further includes a fiber optic rotating junction within the housing having a stationary portion with a stationary fiber therein and a rotatable portion with a rotatable fiber therein. The drive assembly includes a first optical connection through the housing configured to connect the stationary fiber with a light source. The drive assembly includes a motor within the housing configured to rotate the rotatable portion of the fiber optic rotating junction. The drive assembly includes a second optical connection through the housing configured to connect the rotatable portion of the fiber optic rotating junction with both the drive shaft and the rotatable fiber of the imaging catheter so as to transmit torque from the motor to the drive shaft and the rotatable fiber of the catheter and so as to transmit light from the light source to the rotatable fiber of the catheter. The housing is less than 75 cubic inches in volume, and the drive assembly has a total weight of less than 2 pounds.

This and other embodiments can include one or more of the following features. The volume can be less than 40 cubic inches. The volume can be less than 20 cubic inches. The drive assembly can further include a locking mechanism configured to lock a handle of the imaging catheter to the drive assembly. The stationary and rotatable fibers can be configured to transmit an optical coherence tomography signal.

In general, in one embodiment, a drive assembly for driving an imaging catheter having a rotatable fiber and a rotatable drive shaft includes a fiber optic rotating junction having a stationary portion with a stationary fiber therein and a rotatable portion with a rotatable fiber therein. The drive assembly includes a first optical connection configured to connect the stationary fiber with a light source. The drive assembly includes a motor configured to rotate the rotatable portion of the fiber optic rotating junction. The motor has a hollow shaft configured to house a portion of the fiber optic rotating junction such that the motor and the fiber optical rotating junction are coaxial. The drive assembly includes a second optical connection configured to connect the rotatable portion of the fiber optic rotating junction with both the drive shaft and the rotatable fiber of the imaging catheter so as to transmit torque from the motor to the drive shaft and the rotatable fiber of the catheter and so as to transmit light from the light source to the rotatable fiber of the catheter.

This and other embodiments can include one or more of the following features. The rotatable fiber of the fiber optic junction can be housed within the hollow shaft. The drive assembly can further include a locking mechanism that can be configured to lock a handle of the imaging catheter to the drive assembly. The stationary and rotatable fibers can be configured to transmit an optical coherence tomography signal.

In general, in one embodiment, a drive assembly for driving an imaging catheter having a rotatable fiber and a rotatable drive shaft includes a drive assembly housing. The drive assembly further includes a fiber optic rotating junction within the housing having a stationary portion with a stationary fiber therein and a rotatable portion with a rotatable fiber therein. The drive assembly includes a first optical connection through the housing configured to connect the stationary fiber with a light source. The drive assembly includes a motor in the housing configured to rotate the rotatable portion of the fiber optic rotating junction. The drive assembly includes a linear slide in the housing configured to translate the fiber optic rotating junction axially within the housing. The drive assembly includes a second optical connection through the housing configured to connect the rotatable portion of the fiber optic rotating junction with both the drive shaft and the rotatable fiber of the imaging catheter so as to transmit torque from the motor to the drive shaft and the rotatable fiber and so as to transmit light from the light source to the rotatable fiber of the catheter.

This and other embodiments can include one or more of the following features. The stationary fiber of the fiber optic rotating junction can be axially fixed at the first optical connection. The stationary fiber of the fiber optic rotating junction can include slack configured to account for translation of the fiber optic rotating junction. The drive assembly can further include a locking mechanism that can be configured to lock a handle of the imaging catheter to the drive assembly. The stationary and rotatable fibers can be configured to transmit an optical coherence tomography signal.

In general, in one embodiment, a drive assembly for driving an imaging catheter having a rotatable fiber and a rotatable drive shaft, includes a fiber optic rotating junction having a stationary portion with a stationary fiber therein and a rotatable portion with a rotatable fiber therein. The drive assembly includes a first optical connection configured to connect the stationary fiber with a light source. The drive assembly includes a motor configured to rotate the rotatable portion of the fiber optic rotating junction. The drive assembly includes a second optical connection configured to connect the rotatable portion of the fiber optic rotating junction with both the drive shaft and the rotatable fiber of the imaging catheter so as to transmit torque from the motor to the drive shaft and the rotatable fiber of the catheter and so as to transmit light from the light source to the rotatable fiber of the catheter. The drive assembly includes a magnetic locking mechanism configured to automatically align the second optical connection with the drive shaft and the rotatable fiber of the imaging catheter.

Methods of using these drive systems are also described herein.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Described herein are reusable drive assemblies configured to be attached to an imaging catheter, such as an atherectomy catheter. In general, the drive assemblies can include a motor to rotate both a drive shaft of the catheter and a rotating fiber of the catheter. The drive assemblies herein can further include an optical pass-through to transfer light from a light source to the rotating fiber of the catheter, such as for optical coherence tomography (OCT) imaging. The optical pass-through can include a fiber optic rotating junction having a stationary portion with a stationary fiber therein and a rotatable portion with a rotatable fiber therein. The drive assembles can be configured to attach at the proximal end to a light source and at the distal end to a catheter.

In some embodiments, a drive assembly can be configured to provide rotation of a drive shaft, simultaneous rotation of an optical fiber, translation of the drive shaft, and simultaneous translation of the fiber. Such drive assemblies could be used, for example, with a catheter having an imaging sensor and a cutter that are driven by the same drive shaft where the drive shaft can be translated proximally or distally to pack tissue and/or expose the cutter.

For example, referring to FIGS. 1A-5B, a drive assembly 100 can be configured to provide rotation of a drive shaft, rotation of an optical fiber, translation of the drive shaft, and translation of the fiber of an imaging catheter.

Figure 1A:
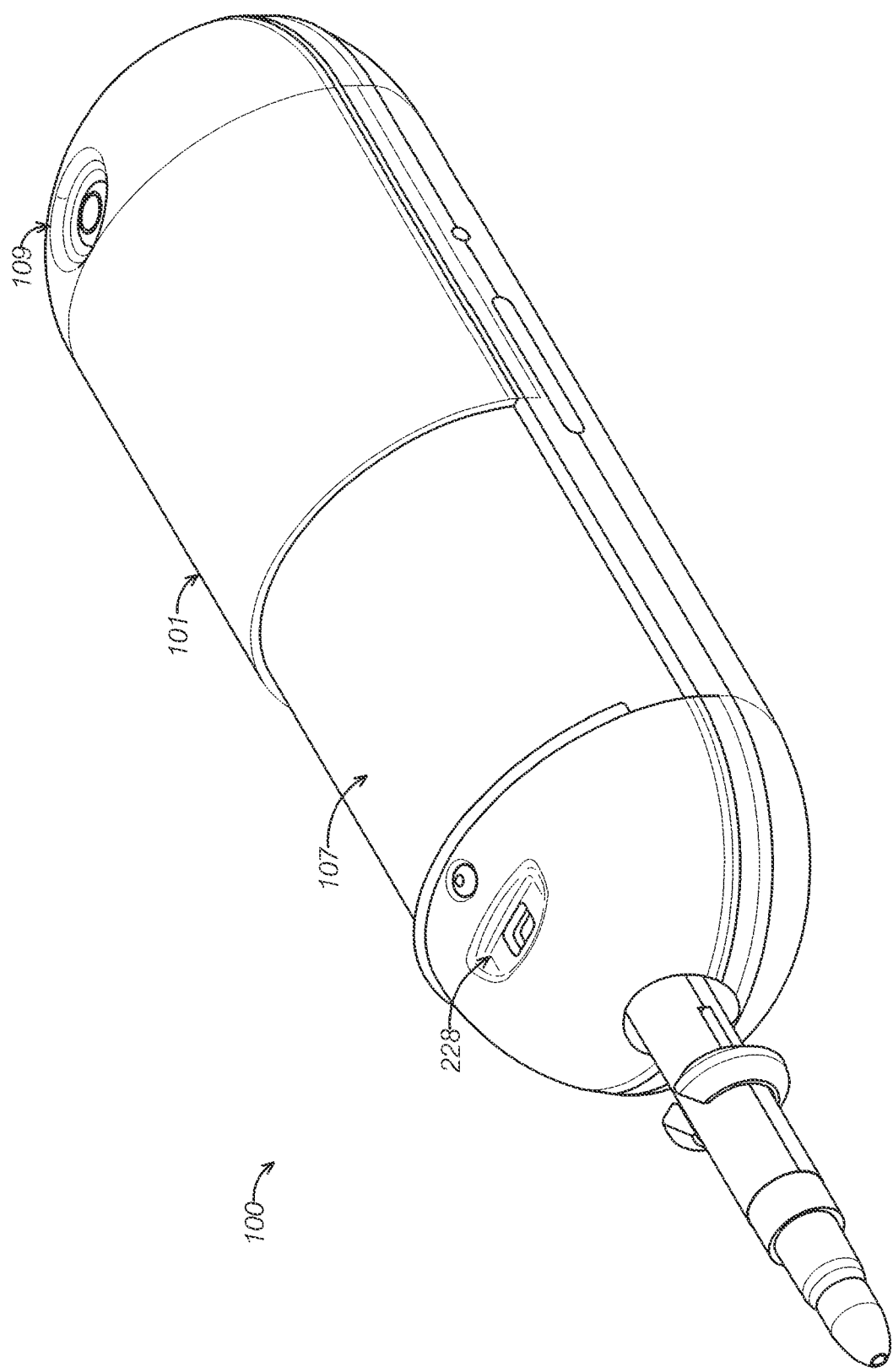
FIG. 1A shows a variation of the drive assembly configured to drive an imaging catheter with a rotary cutter. The drive assembly includes a motor to drive the catheter cutter and a linear slide assembly to translate an optical assembly with a drive shaft.
Figure 1B:
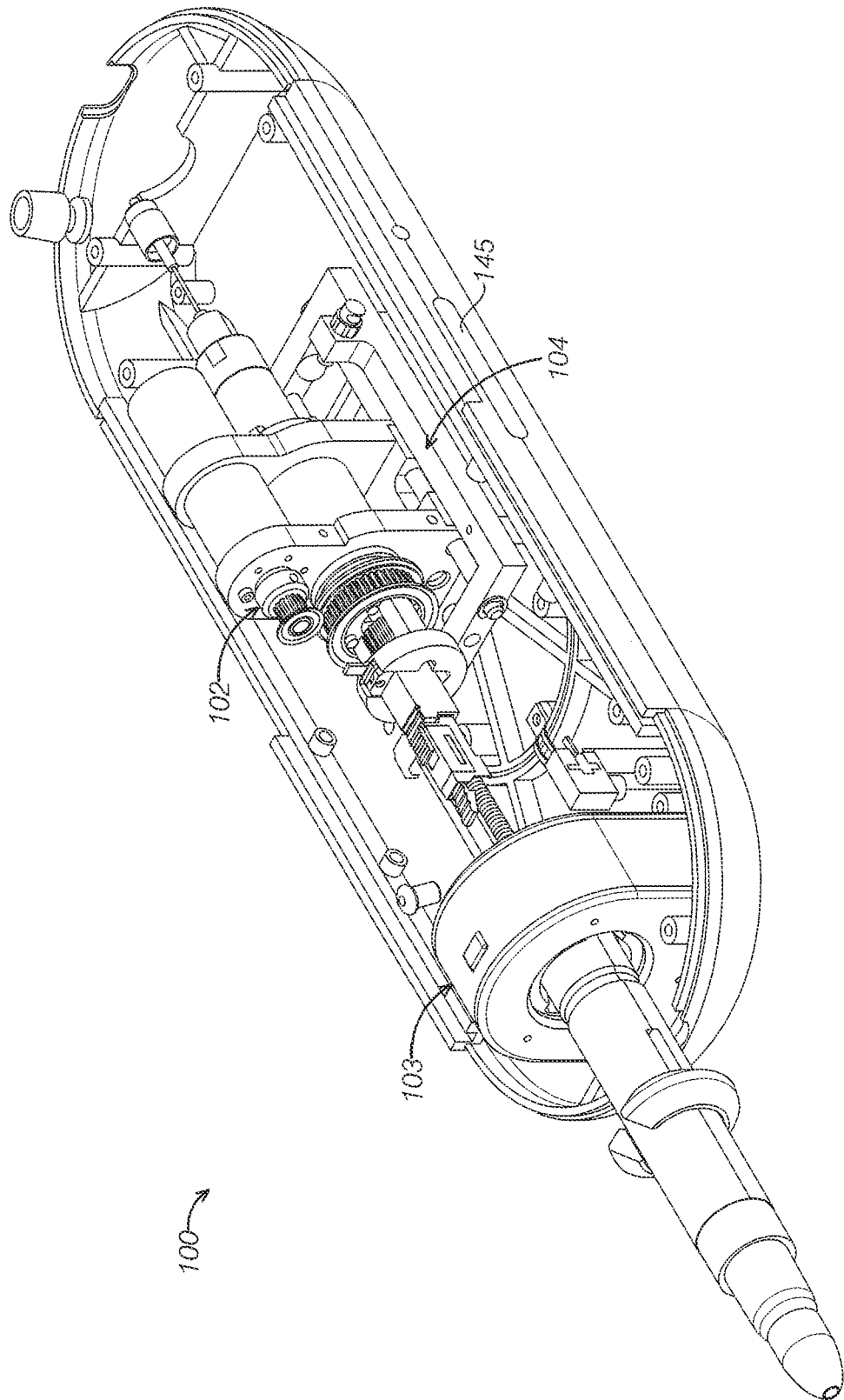
FIG. 1B shows the drive assembly with the outer housing removed to exhibit the interior components.

As shown in FIGS. 1A-1B, the drive assembly 100 can include a housing 101 (having an access door 107 therein) and a handle lock 103, to connect the drive assembly 100 to a catheter handle. As shown in FIG. 1B, the drive assembly 100 can further include a rotary optical drive subassembly 102 configured to provide rotation to the drive shaft and optical fiber of a catheter and a linear slide subassembly 104 configured to provide translation of the drive shaft and optical fiber of the catheter used with the drive assembly 100. The drive assembly 100 can be connected at a proximal end to the light source. A power source can connected to the drive assembly 100 to provide the driving power. A power button 109 can be used to turn the power to turn the drive assembly 100 on and off.

Figure 2B:
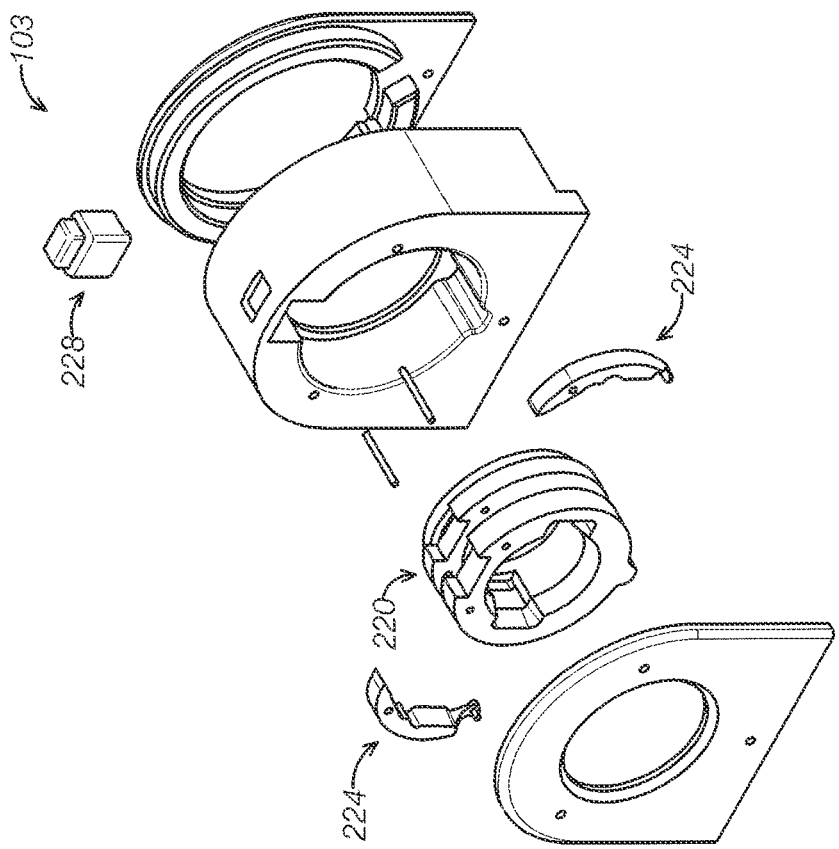
FIG. 2B shows an exploded view of the drive assembly of FIG. 2A.
Figure 2A:
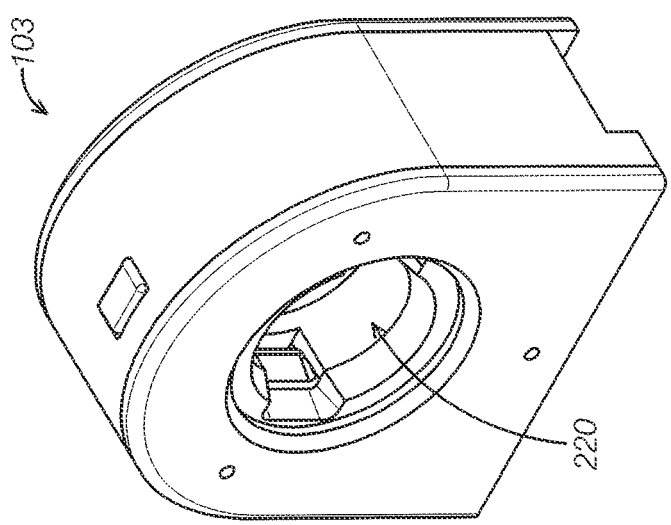
FIG. 2A shows a handle lock of the drive assembly of FIGS. 1A and 1B.

The handle lock 103 can provide a mechanical interface to secure the catheter handle to the drive assembly 100 during use. In one embodiment, as shown in FIG. 2B, the handle lock 103 can include a core 220, two retaining arms 224, and a release button 228 (the release button is also shown in FIG. 1A). The handle lock core 220 can include mating features 229 thereon configured such that the core 220 can mate with the proximal end of the catheter handle and enclose the proximal end of the catheter handle and limit radial handle movement. Axial movement of the catheter handle can be limited by the retaining arms 224 once the handle is fully seated in the lock 103.

Figure 3A:
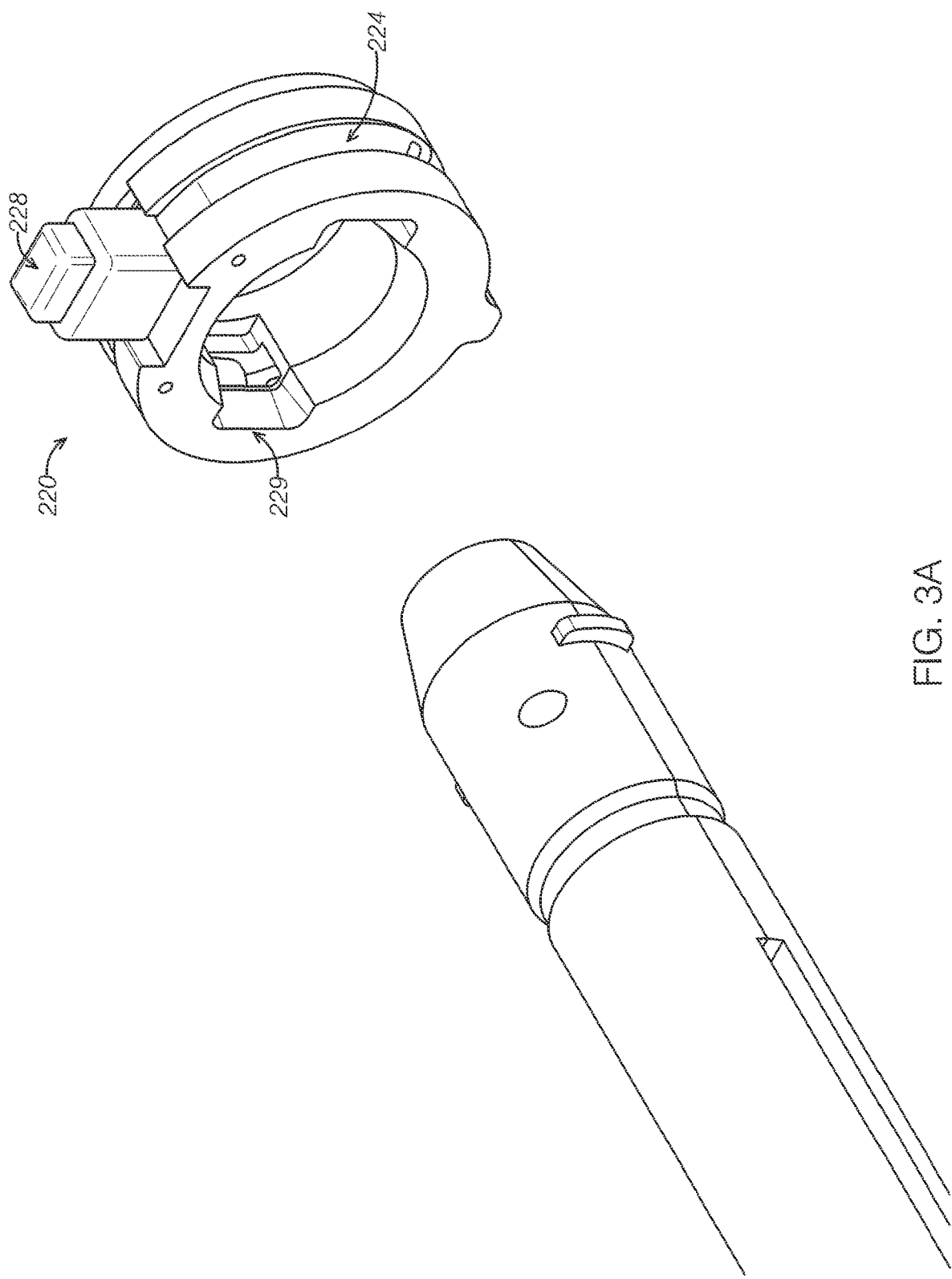
FIG. 3A shows the interaction between the handle lock of FIG. 2A and a catheter handle.
Figure 3C:
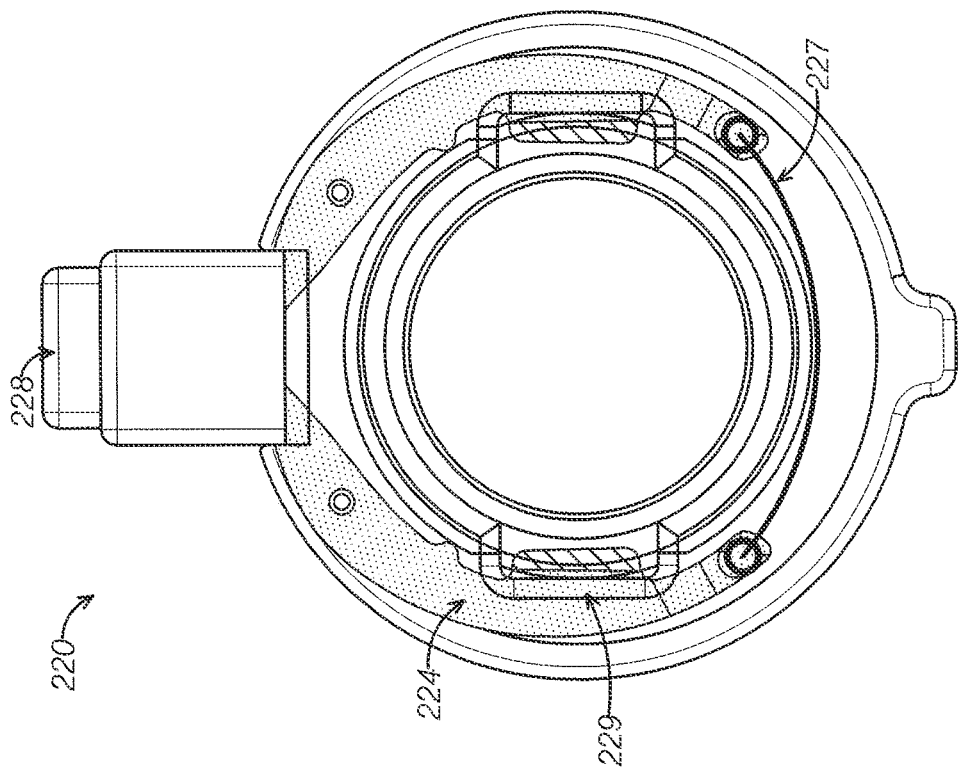
FIG. 3C shows the handle lock of FIG. 2A in a closed position.
Figure 3B:
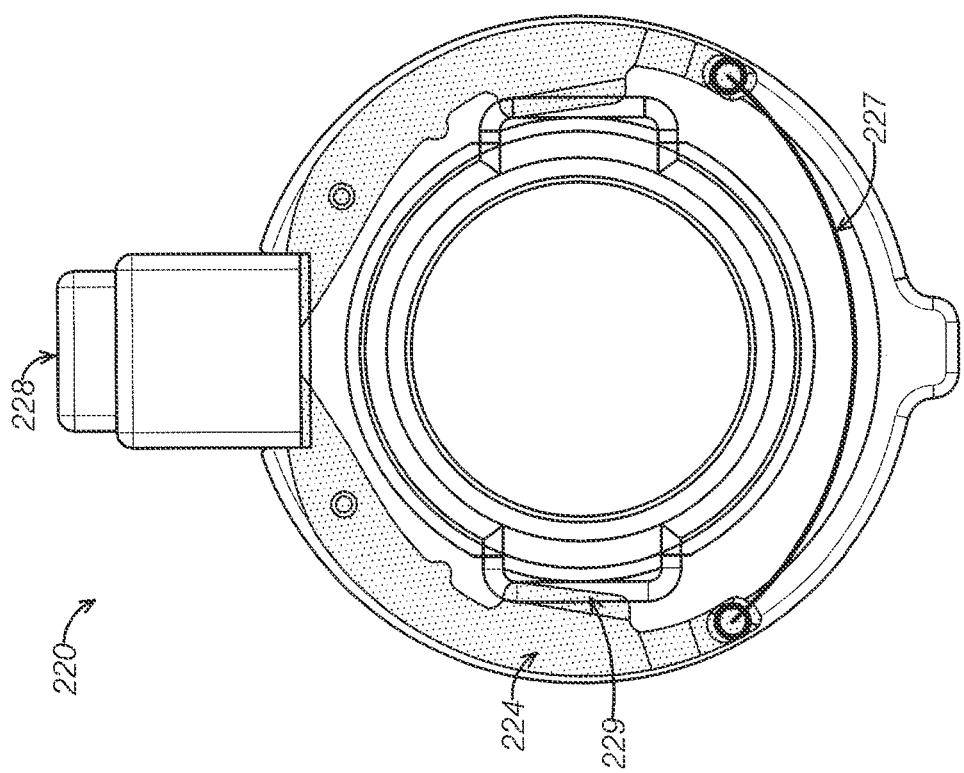
FIG. 3B shows the handle lock of FIG. 2A in an open position.

Referring to FIG. 3A, to engage the retaining arms 224, the handle of the catheter can be inserted into the handle lock 103 such that features of the handle (such as mating wings) fit within the mating keyways 229 of the core 220, thereby allowing for self-alignment of the handle with the drive assembly 100. Once inserted, the handle can push the retaining arms 224 into the open position, as shown in FIG. 3B. After the mating features of the handle, such as wings, pass fully through the retaining arms 224, an extension spring 227 in the handle lock 103 can cause the retaining arms 224 to return to a closed position (see FIG. 3C), preventing the catheter and catheter handle from moving axially and rotationally within the sled. After use, the catheter or catheter handle can be removed from the drive assembly 100 by pushing down on the handle release button 228, which can cause the retaining arms 224 to rotate into the open position, thereby allowing the catheter handle to be removed from the handle lock 103.

Figure 4A:
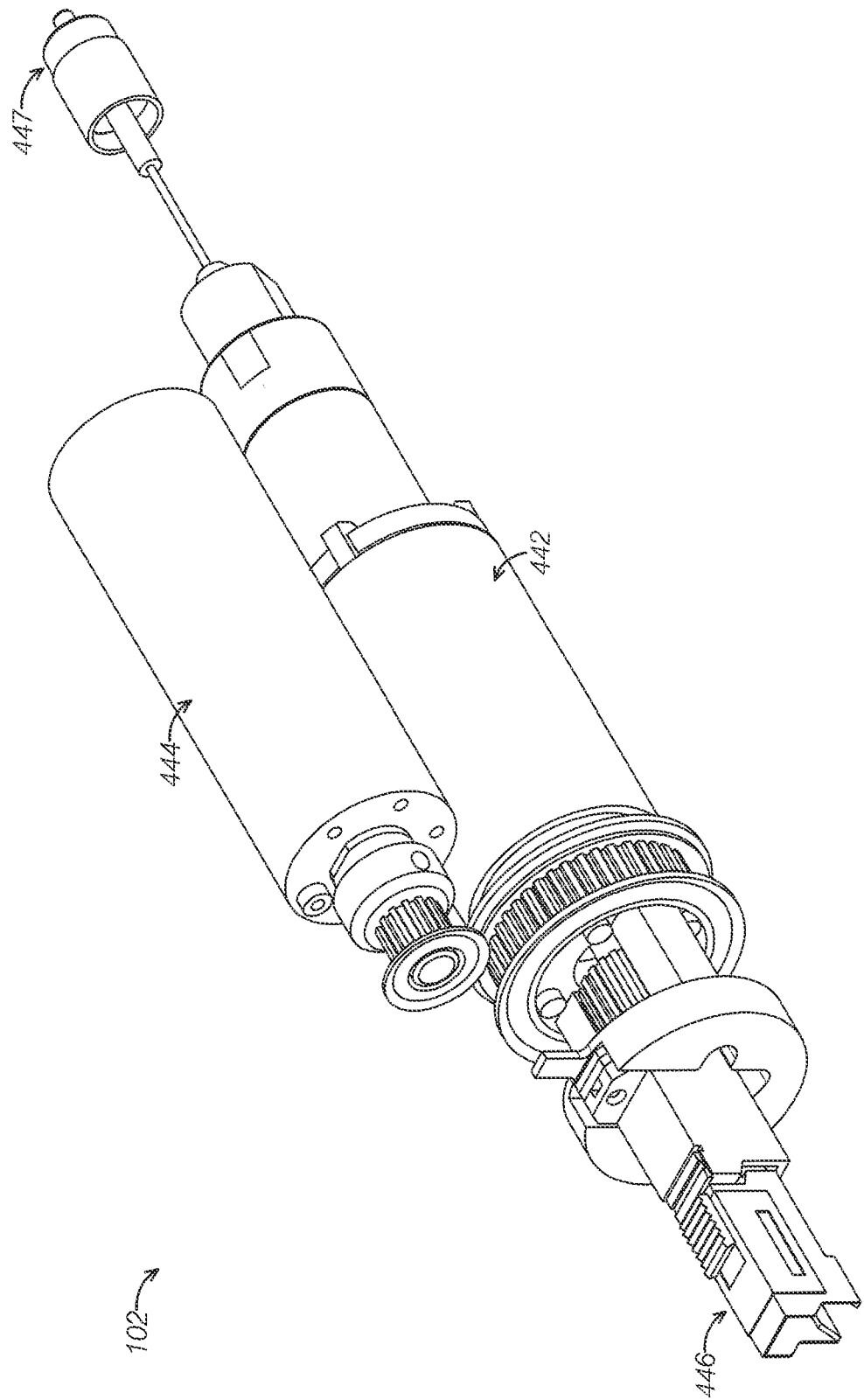
FIGS. 4A and 4B show the rotary optical drive subassembly of the drive assembly of FIGS. 1A and 1B.

Referring to FIG. 4A, the rotary optical drive subassembly 102 of the drive assembly 100 can include a fiber optic rotating junction (FORJ) 442, a motor 444, an optical connector 446, which can be connected to the drive shaft (and optical fiber) of the catheter, and an optical connector 447, which can connected to the light source. The FORJ 442 can advantageously serve to provide an optical link between light from a light source and the optical fiber of the catheter. The FORJ 442 can further advantageously serve to decouple the catheter fiber rotation from light source fiber rotation, i.e., can provide a junction for the catheter's rotating optical fiber and a static optical fiber from the light source. In one embodiment, the motor 444 can be a DC brushless motor with integrated speed controller. In use, the motor 444 can be configured to drive the FORJ through a belt-pulley system. In turn, the FORJ 442 can be configured to drive the rotation of the drive shaft and optical fiber of the catheter through the optical connector 446, which can connect directly to the drive shaft.

Figure 4B:
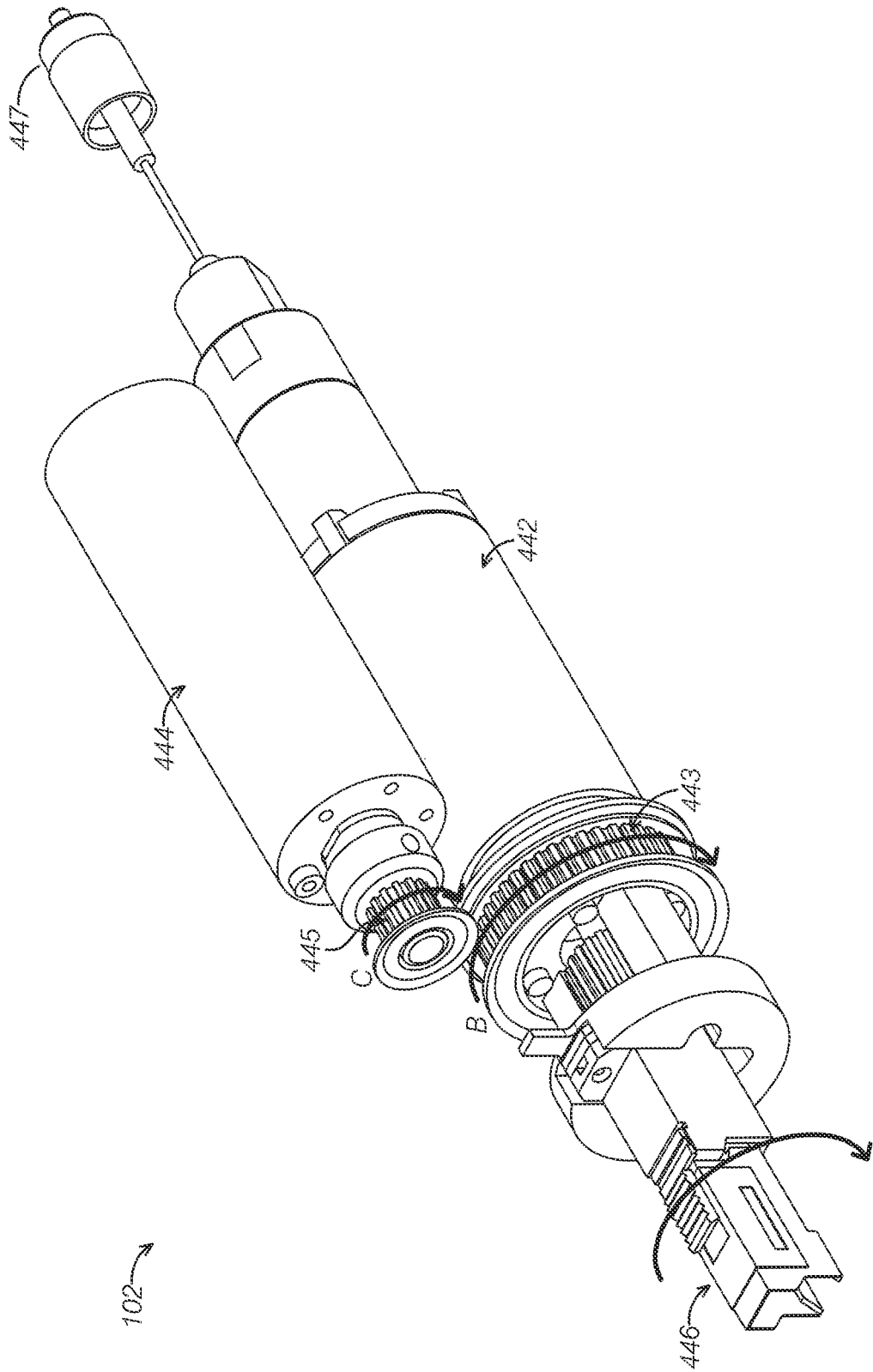

Thus, referring to FIG. 4B, the motor 444 and the FORJ 442 can have pulleys 445, 443, respectively, that can be connected by a belt (not shown). As the motor 444 turns (shown by arrow B), the FORJ 442 turns (shown by arrow C). The FORJ 442 can be rigidly connected to the distal optical connector 446 through mechanical couplings. Therefore, as the FORJ 442 turns, the optical connector 446 turns. When the catheter handle is attached, the distal optical connector is mechanically locked to the catheter optical connector, which is connected to the drive shaft and optical fiber of the catheter. Therefore, as the distal optical connector 446 rotates, so does the catheter drive shaft and optical fiber.

Figure 5A:
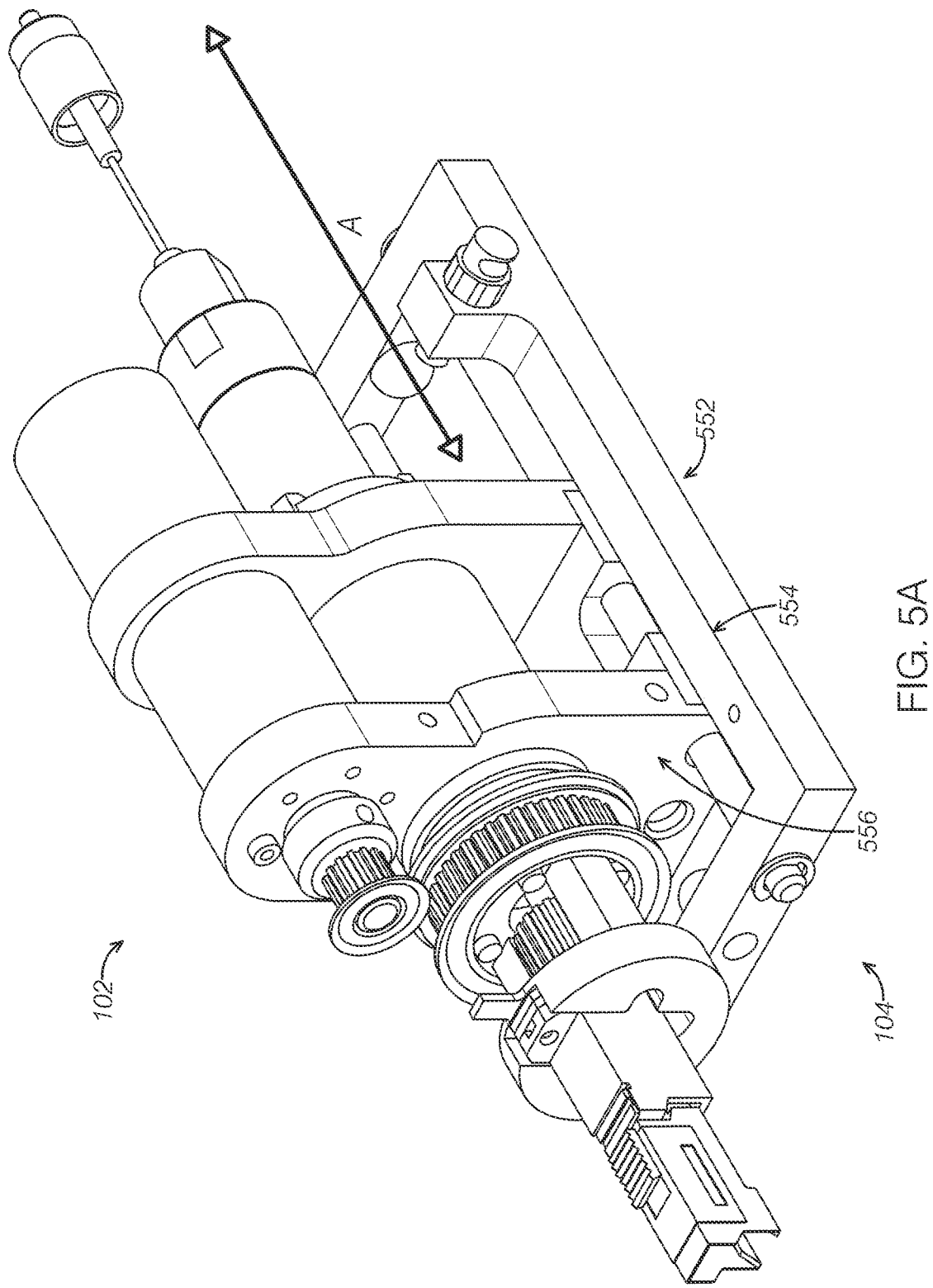
FIG. 5A shows activation of the linear slide of the rotary optical drive subassembly of FIGS. 4A and 4B in a tissue packing position.
Figure 5B:
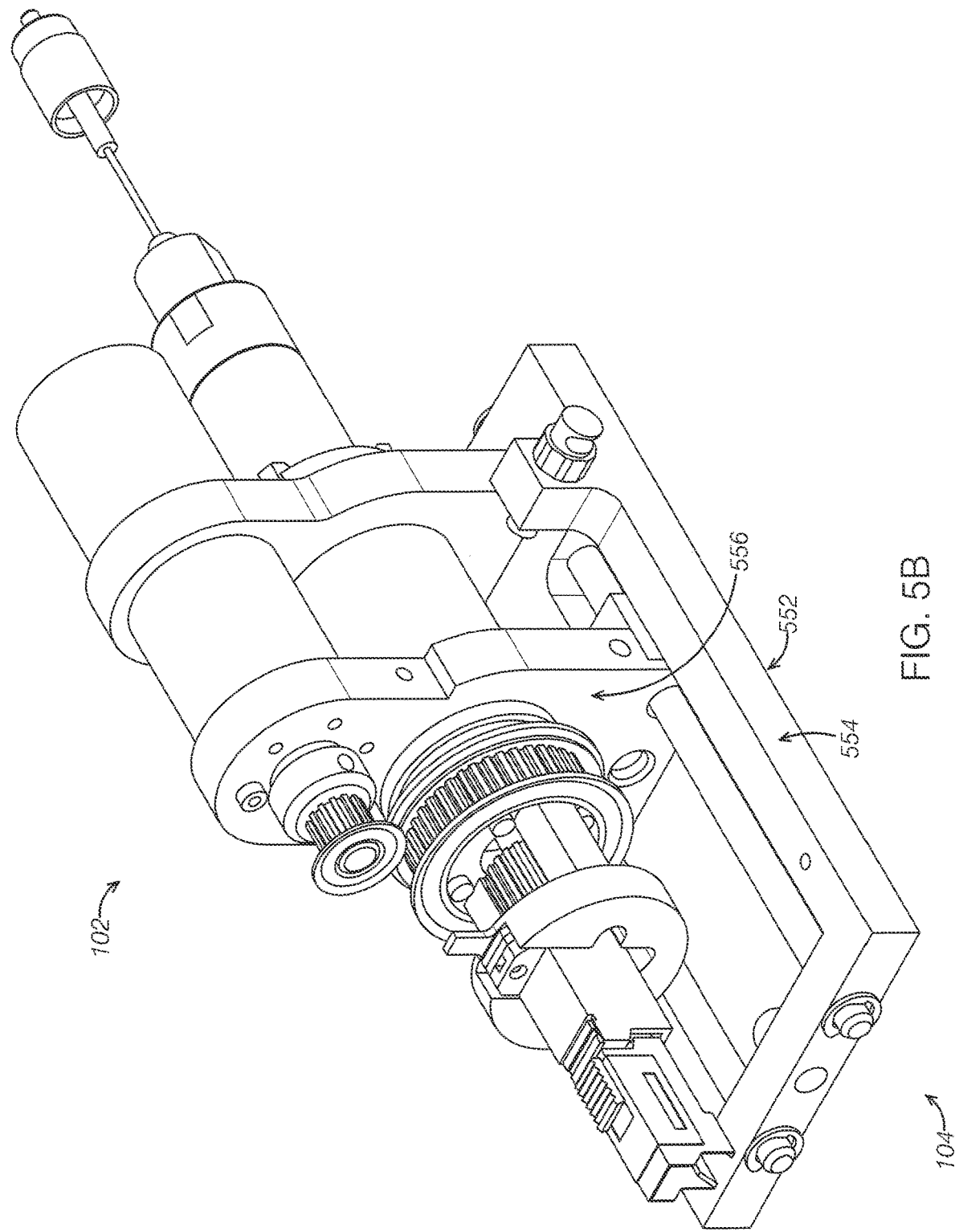
FIG. 5B shows activation of the linear slide of the rotary optical drive subassembly of FIGS. 4A and 4B in a tissue cut position.

Referring to FIGS. 5A and 5B, the linear slide subassembly 104 includes a linear slide 552 having a stationary portion 554 connected to the housing 101 of the drive assembly 100 and a translatable portion 556 movable relative to the housing 101 of the drive assembly. The rotary optical drive subassembly 102 can rest on, and be fixedly attached to, the translatable portion 556 of the linear slide 552. As a result, the rotary optical drive subassembly 102 can slide axially (proximally and distally) relative to the stationary portion 554 of the linear slide 552 (and thus relative to the housing 101), as shown by the arrow A in FIG. 5A. The linear slide assembly can thus translate axially in concert with axial movement of the catheter's drive shaft and optical fiber (such as for exposing the cutter or packing the nosecone). Thus, as shown in FIGS. 5A and B, if the drive shaft and thus the cutter need to be moved distally (FIG. 5A) and/or proximally (FIG. 5B), such as to activate the nosecone or cutter deflection and/or pack tissue into the nosecone, the rotary optical subassembly 102 can move simultaneously, thereby maintaining the optical connection between the catheter and the light source.

The linear slide can include a space for slack in the optical fiber therein. For example, slack in the optical fiber can coil around within the inner perimeter of the housing 101. The slack in the optical fiber can ensure that movement of the rotary optical subassembly 102 distally will not pull the optical fiber out of the optical connection 447 with the light source (as the optical fiber can be axially fixed at the optical connection 447).

In some embodiments, movement of the rotary optical subassembly 102 can be activated through the optical connection 446 via an activation mechanism on the handle or the catheter. Thus, the rotary optical subassembly 102 can be passively moved as the parts of the catheter or handle are actively moved. A release lever 145 can be configured to either allow or restrict the rotary optical subassembly 102 from translating (thereby providing a locking mechanism to hold the rotary optical subassembly 102 in place when desired).

The axial translation of the rotary optical drive assembly 104 and the drive shaft can occur relative to the sled housing 101 and the catheter outer shaft and handle (connected to the housing 101), all of which can remain stationary. Maintaining a stationary outer shaft ensures that the outer shaft can remain axially and rotationally stabilized in the vessel while the cutter deflection and/or tissue packing occur, thereby ensuring that the physician does not lose the desired catheter position relative to the vessel.

The drive assembly 100 can advantageously provide a therapeutic amount of torque to the drive shaft/cutter of a catheter while also providing the required speed of rotation for imaging, such as OCT imaging. For example, the drive assembly 100 can provide 0.5 to 15 ounce inches of torque, such as 0.5 to 10 ounce inches, such as 1 to 5 ounce inches, such as approximately 2 ounce inches of torque.

In some embodiments, a drive assembly can be configured to provide only rotation of a drive shaft and simultaneous rotation of an optical fiber (and not translation of either). Such drive assemblies could be used, for example, with: (1) a catheter having an imaging sensor and a cutter that are driven by the same drive shaft where the drive shaft can be translated proximally or distally to pack tissue and/or expose the cutter (and where the translation mechanism is provided in the handle); or (2) a catheter having a separately rotatable imaging and cutting shaft.

For example, the drive assembly 100 described above can be used without the linear drive subassembly 102 to provide only rotation. Another drive assembly 1400 is shown with respect to FIGS. 6-15 that can be configured to provide rotation of a drive shaft and rotation of an optical fiber of an imaging catheter.

Figure 6:
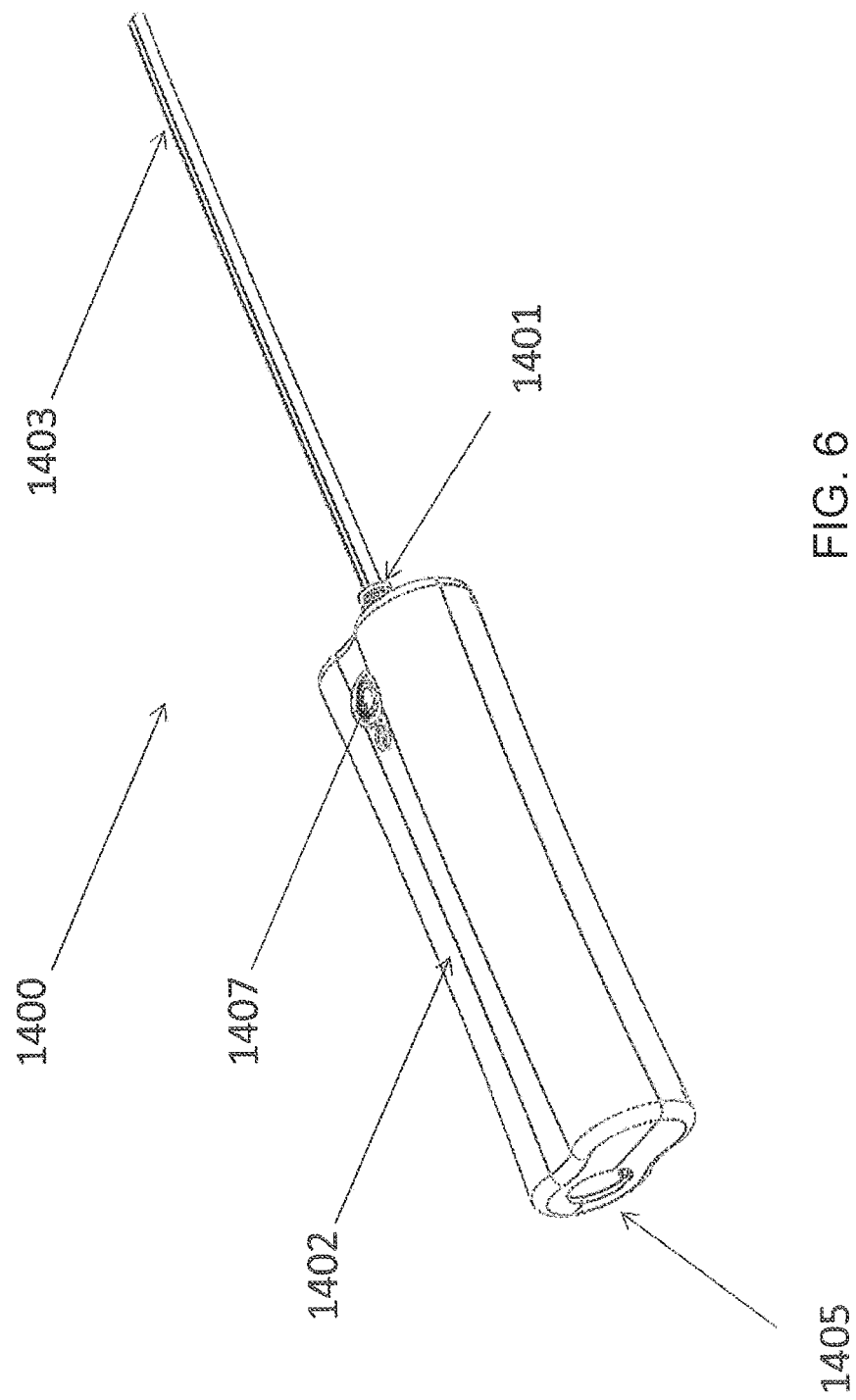
FIG. 6 shows the outer housing of another exemplary drive assembly.
Figure 7:
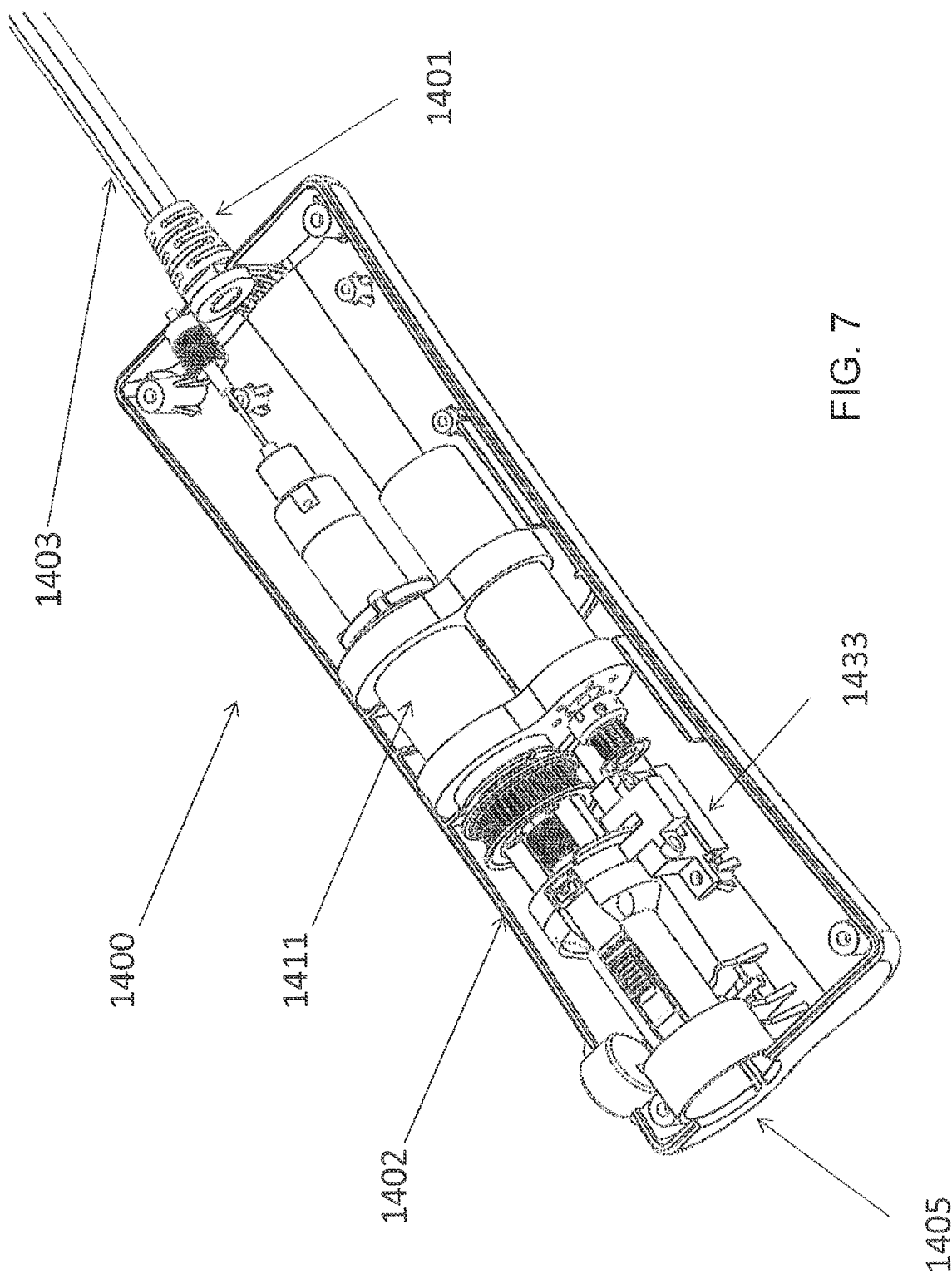
FIGS. 7 and 8 show the drive assembly of FIG. 6 with the housing removed to show the inner components and subassemblies.
Figure 8:
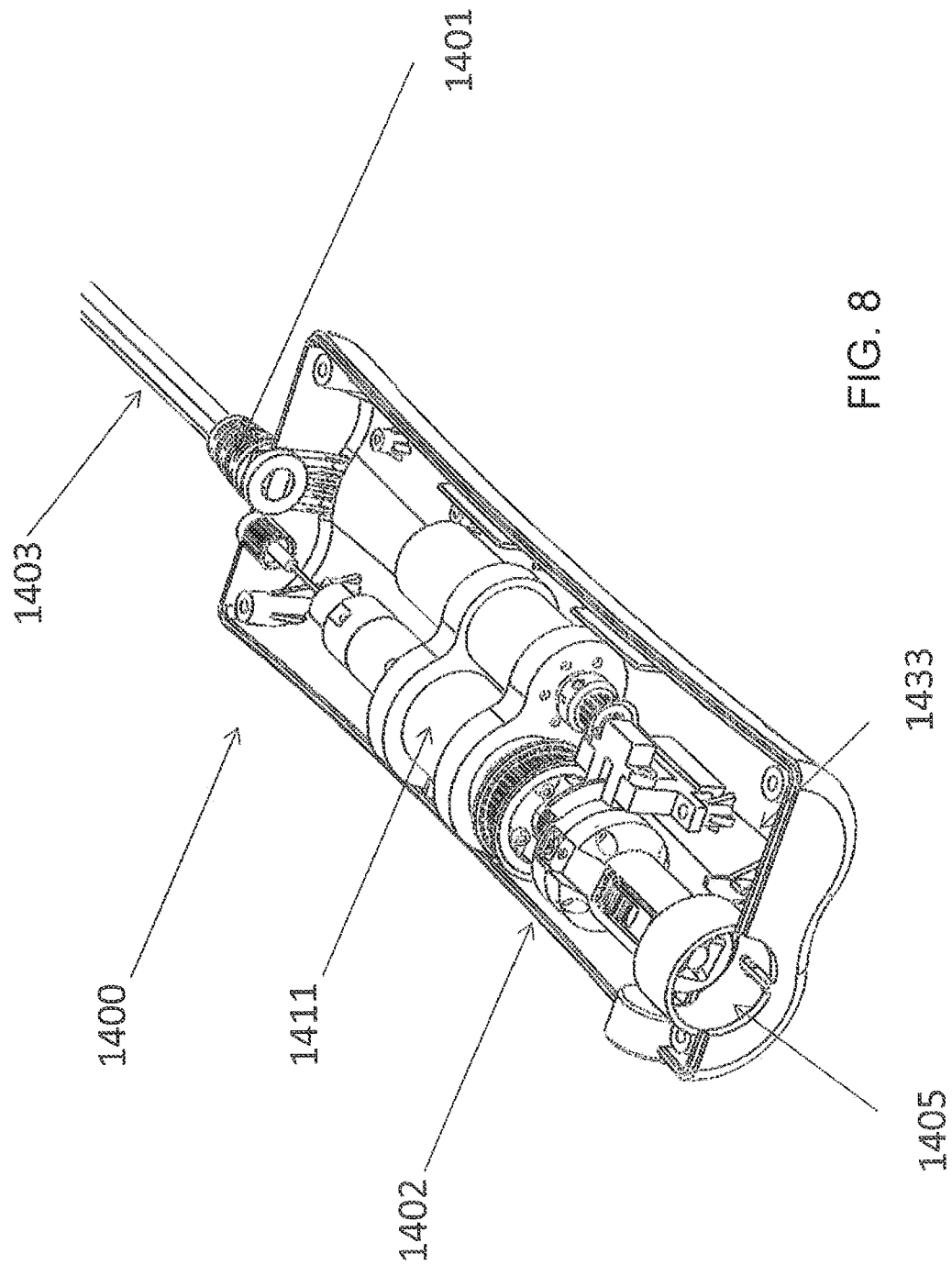
Figure 9:
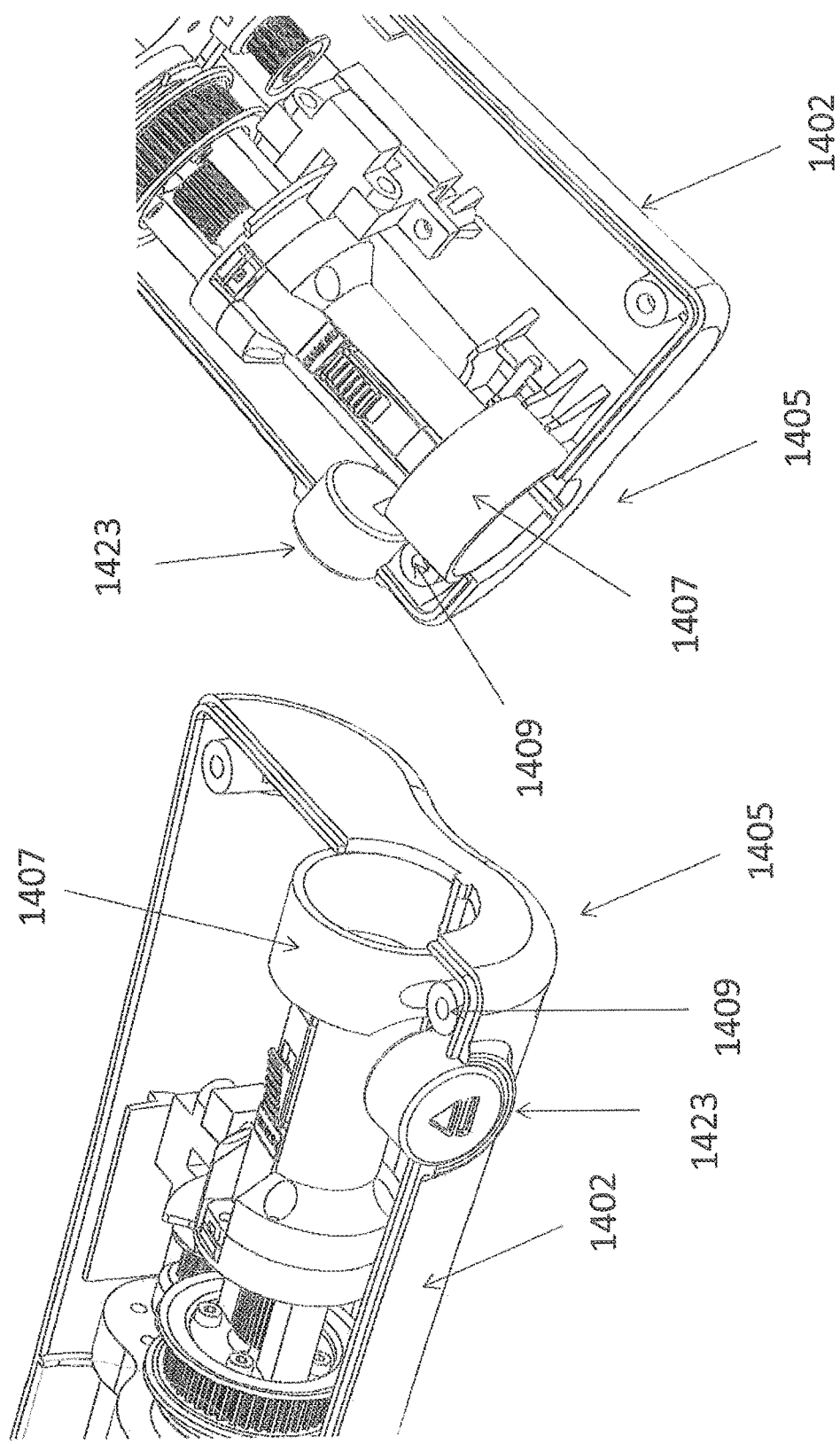
FIGS. 9A and 9B show a close-up of the distal portion of the drive assembly shown in FIGS. 7 and 8, including the locking mechanism to connect a handle to the drive assembly of FIG. 6.
Figure 10:
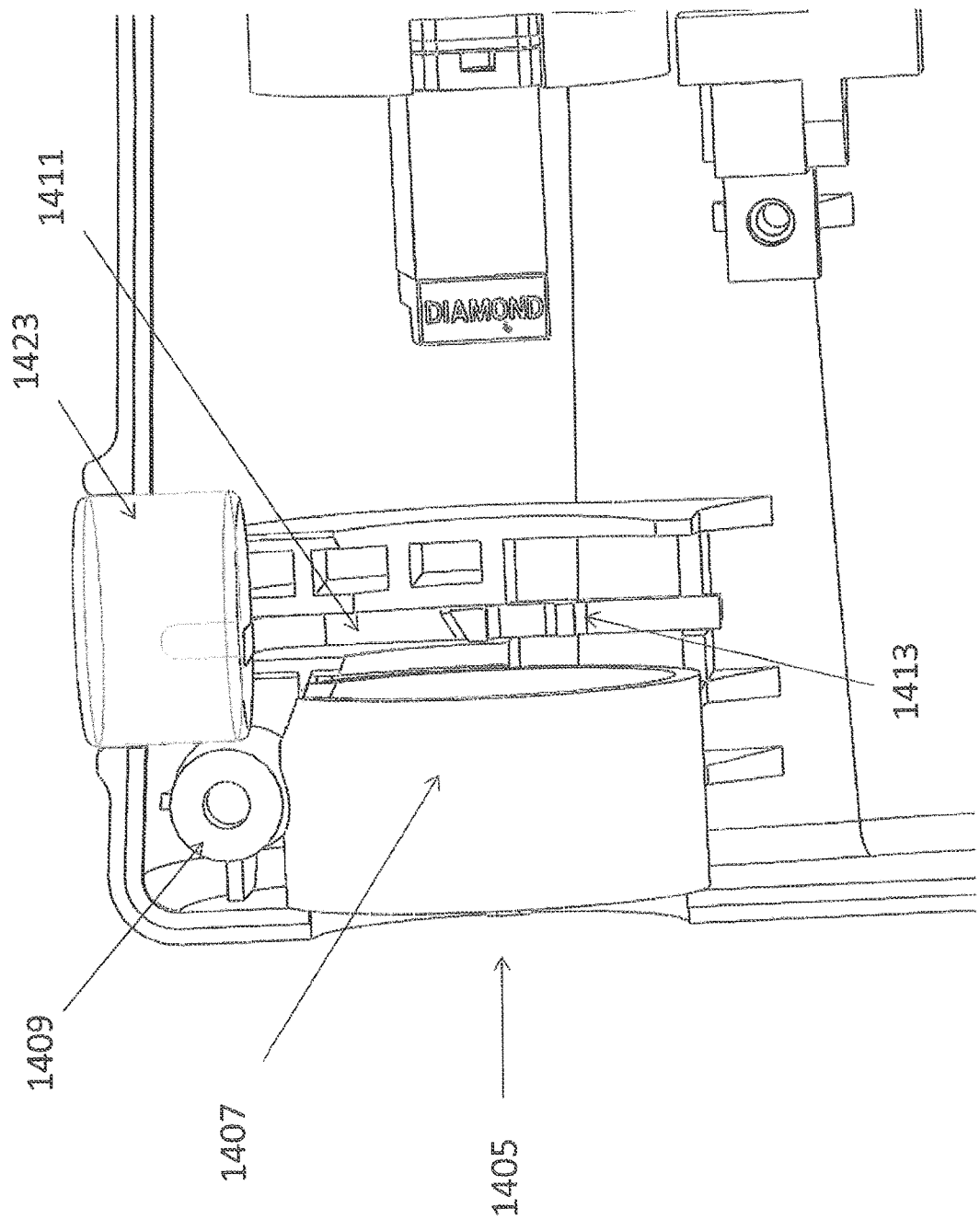
FIG. 10 is a top view of the locking mechanism of FIGS. 7 and 8.
Figure 11A:
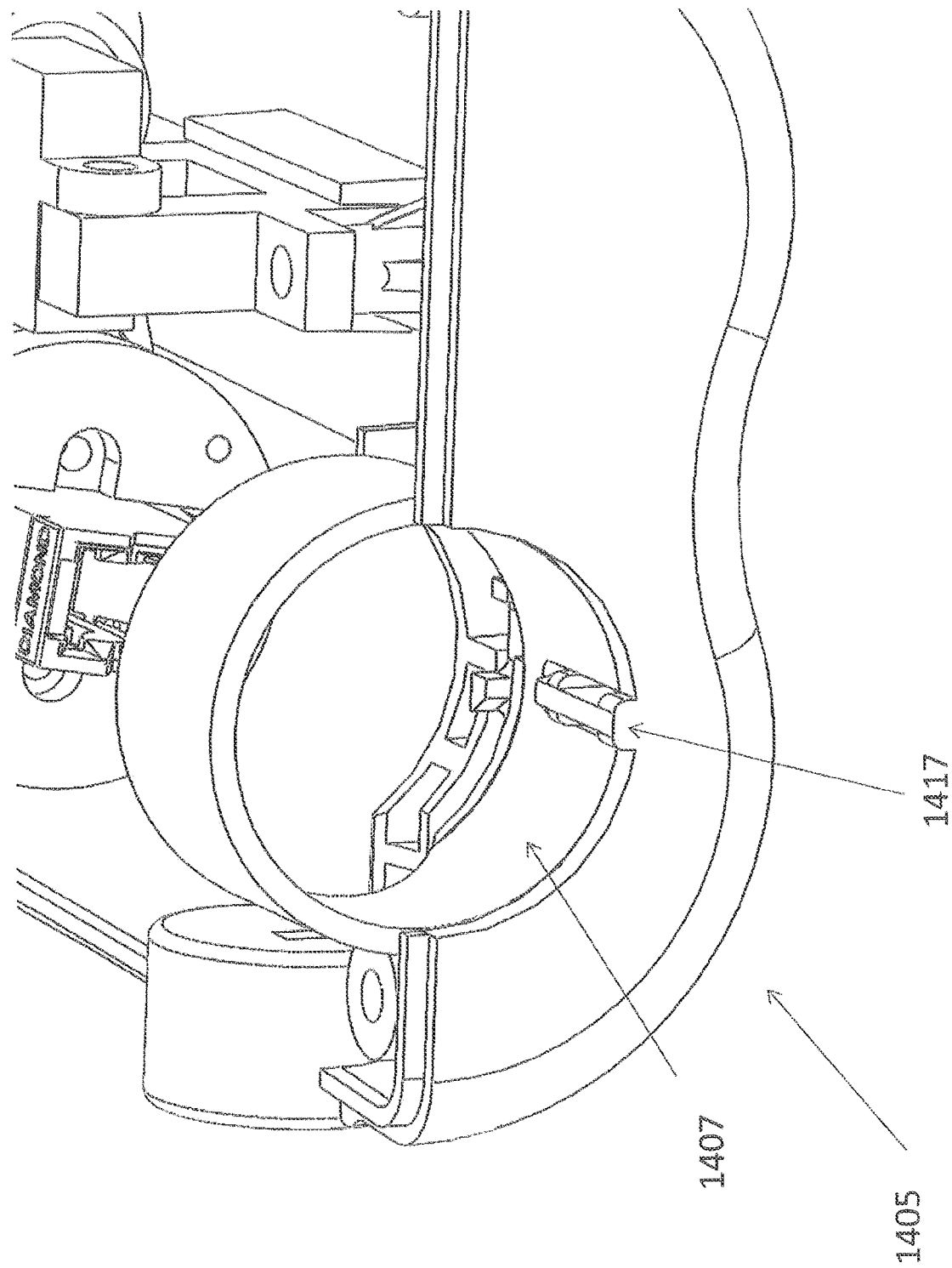
FIGS. 11A and 11B show front and side view of the locking mechanism of FIGS. 7 and 8.
Figure 11B:
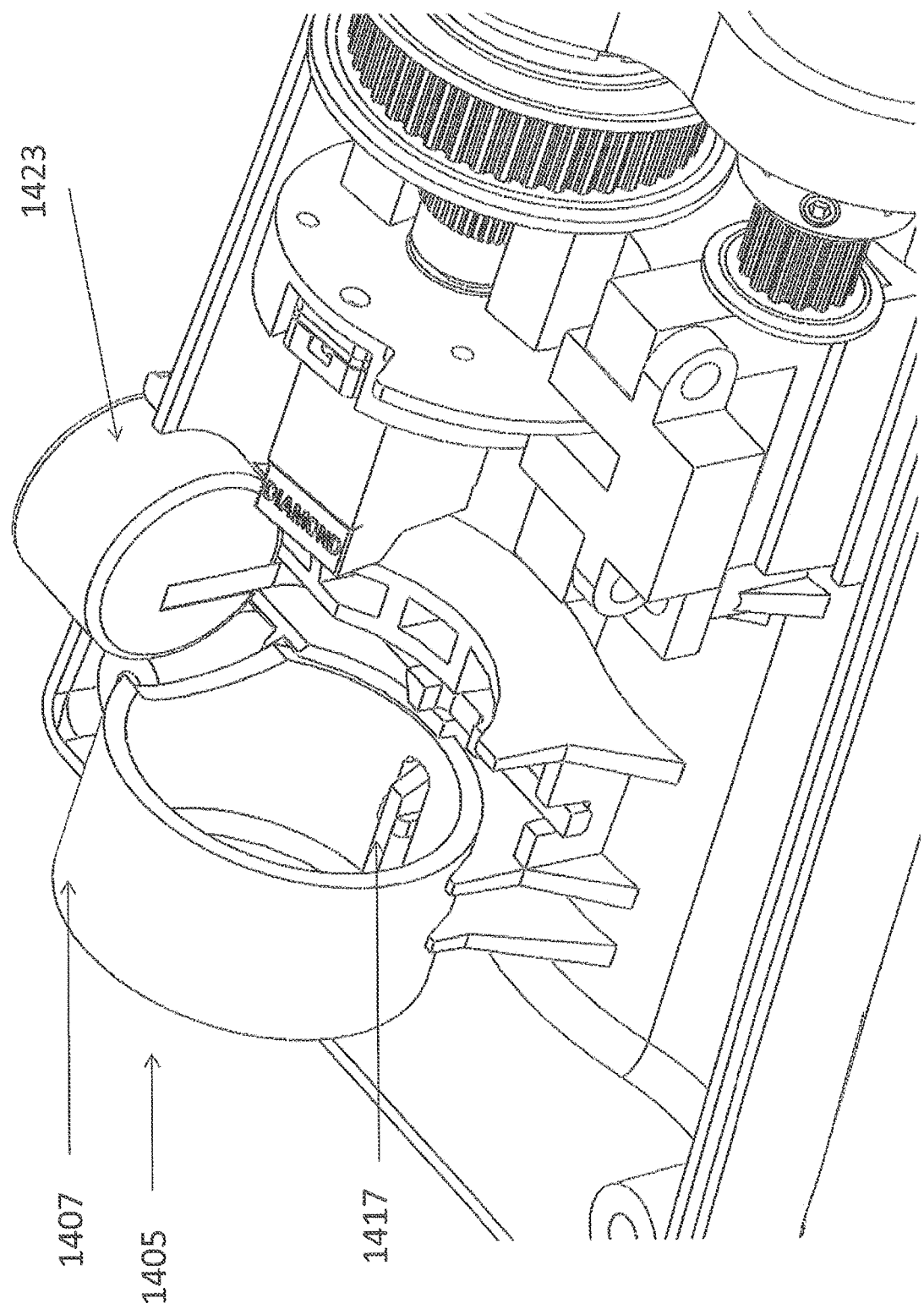

Referring to FIGS. 6-8, the drive assembly 1400 can include a housing 1402 having a rotary optical subassembly 1411, a control board (not shown), and a position sensor 1433 therein. The drive assembly 1400 can further include a connection 1401 to a cable 1403 extending to the light source as well as a handle lock 1405 to connect to a catheter handle. A power button 1407 on the housing 1402 can be used to toggle power to the drive assembly 1400.

Referring to FIGS. 9A-11B, the handle lock 1405 can be a mechanical interface which secures a catheter handle of an imaging catheter to the drive assembly 1400 during use. The handle lock 1405 can include a core 1407 to limit radial handle movement by encircling the proximal end of the catheter handle. The core 1407 can be held in place in the drive assembly 1400 by mating features 1409 at the top and bottom of the housing 1402. The catheter handle can be locked in its axial position by a handle lock bar 1411 that is loaded with a spring 1413. To lock the handle into the drive assembly 100, mating feature (such as a wing) on the handle is aligned with a mating keyway 1417. When inserting the catheter into the drive assembly, the keyway 1415 on the handle initially aligns the spring-loaded handle lock bar boss 1419 with the keyway 1417, thereby allowing g for self-alignment of the handle with the drive assembly 1400. As the handle is inserted further, the handle lock bar boss 1419 eventually slides into a locking channel 1421 on the handle, securing the handle position. To release the handle, the user pushes the handle release button 1423, which can be attached to the handle lock bar 1411. As a result, the handle lock bar 1411 slides back into alignment with the keyway 1417, allowing the handle to be removed. Movement of the handle lock bar 1411 and button 1423 is otherwise restrained by the housing 1402.

Figure 12:
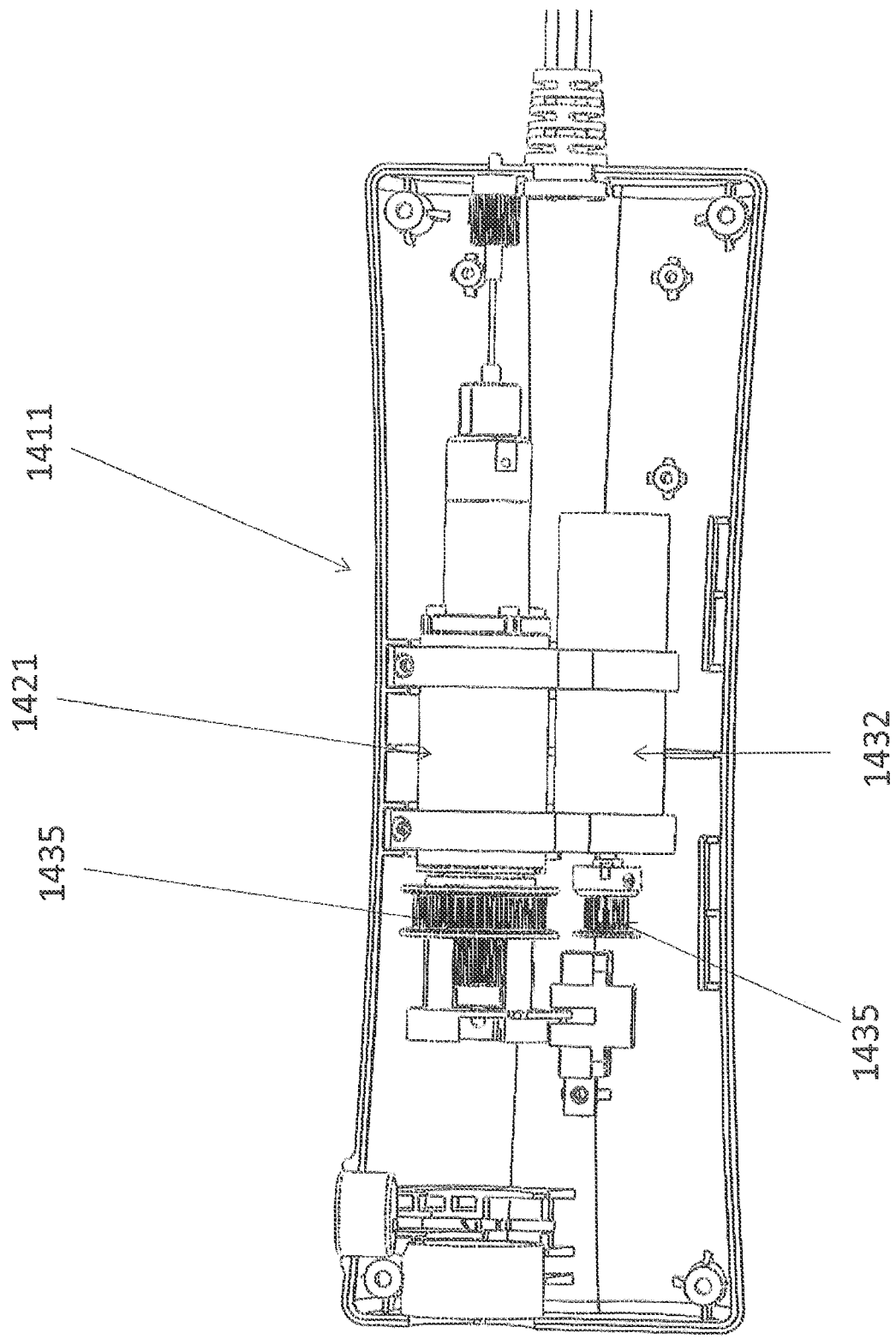
FIGS. 12 and 13 show the drive assembly of FIGS. 7 and 8, including an exemplary rotary optical drive assembly.
Figure 13:
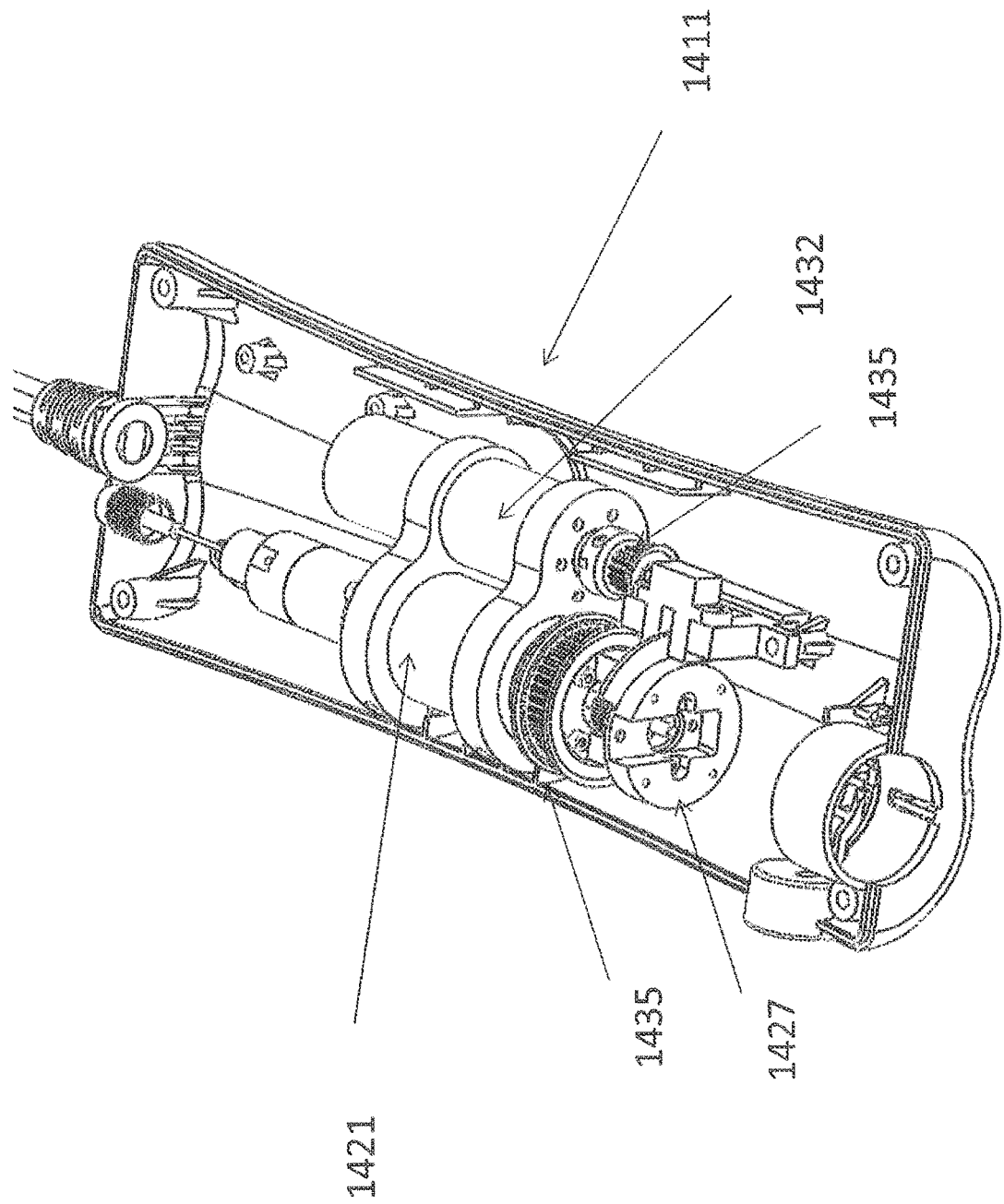

Referring to FIGS. 12-13, the rotary optical subassembly 1411 includes a fiber optic rotating junction (FORJ) 1421 and a motor 1432, such as a DC brushless motor with integrated speed control. The rotary optical subassembly 1411 can be designed similar to the rotary optical subassembly 102 described above and can thus serve to both: (1) decouple the catheter fiber rotation from the source of rotation; and (2) drive the catheter's cutting and imaging elements through the optical connector 1427. The motor 1432 drives the FORJ 1421 through pulleys 1431, 1435 which are connected by a belt (not shown). In turn, the FORJ 1421 drives the rotation of the drive shaft and optical fiber of the catheter through the optical connector 1427.

The drive assembly 1400 can further include an automatic alignment feature to align the catheter properly with respect to the drive assembly 1400. Cleaving the optical fiber of the catheter and the optical fiber of the drive assembly at an angle (e.g. 8 degrees) is desirable to reduce back-reflection at the interface between the optical fibers. Immediate physical connection is also desirable to reduce transmission losses. As such, the optical fibers should be aligned at exactly the right orientation (with the angled cleaves lined up) to allow the light to travel from one optical fiber). If an automatic alignment feature is created to properly orient these fibers with respect to one another, then the separate step of manually connecting the optical assemblies of the catheter/handle and the drive assembly can be eliminated.

Figure 14A:
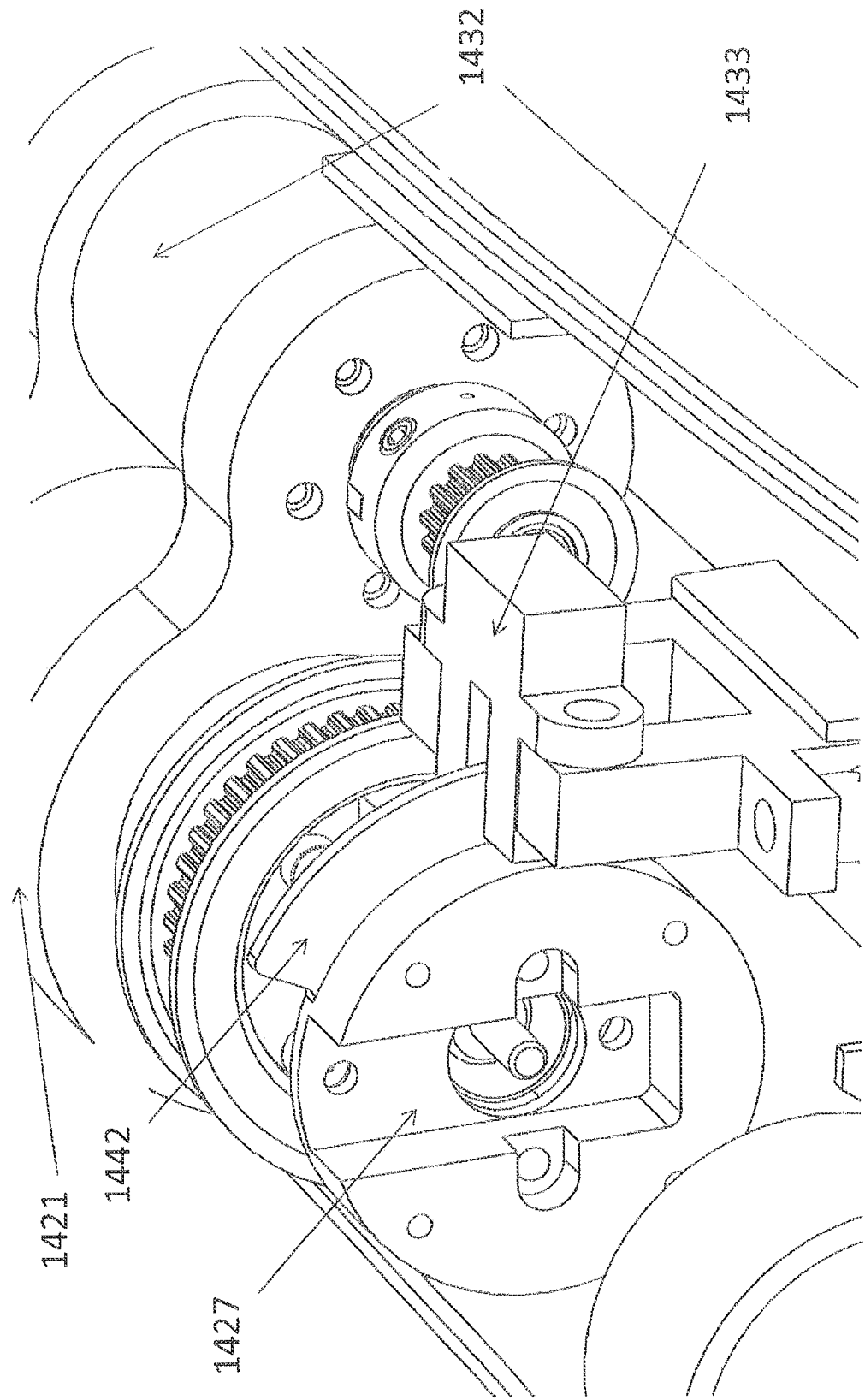
FIGS. 14A and 14B show a close-up of an optical sensor configured to align a drive assembly (such as the drive assembly of FIGS. 7 and 8) with a catheter or catheter handle.
Figure 14B:
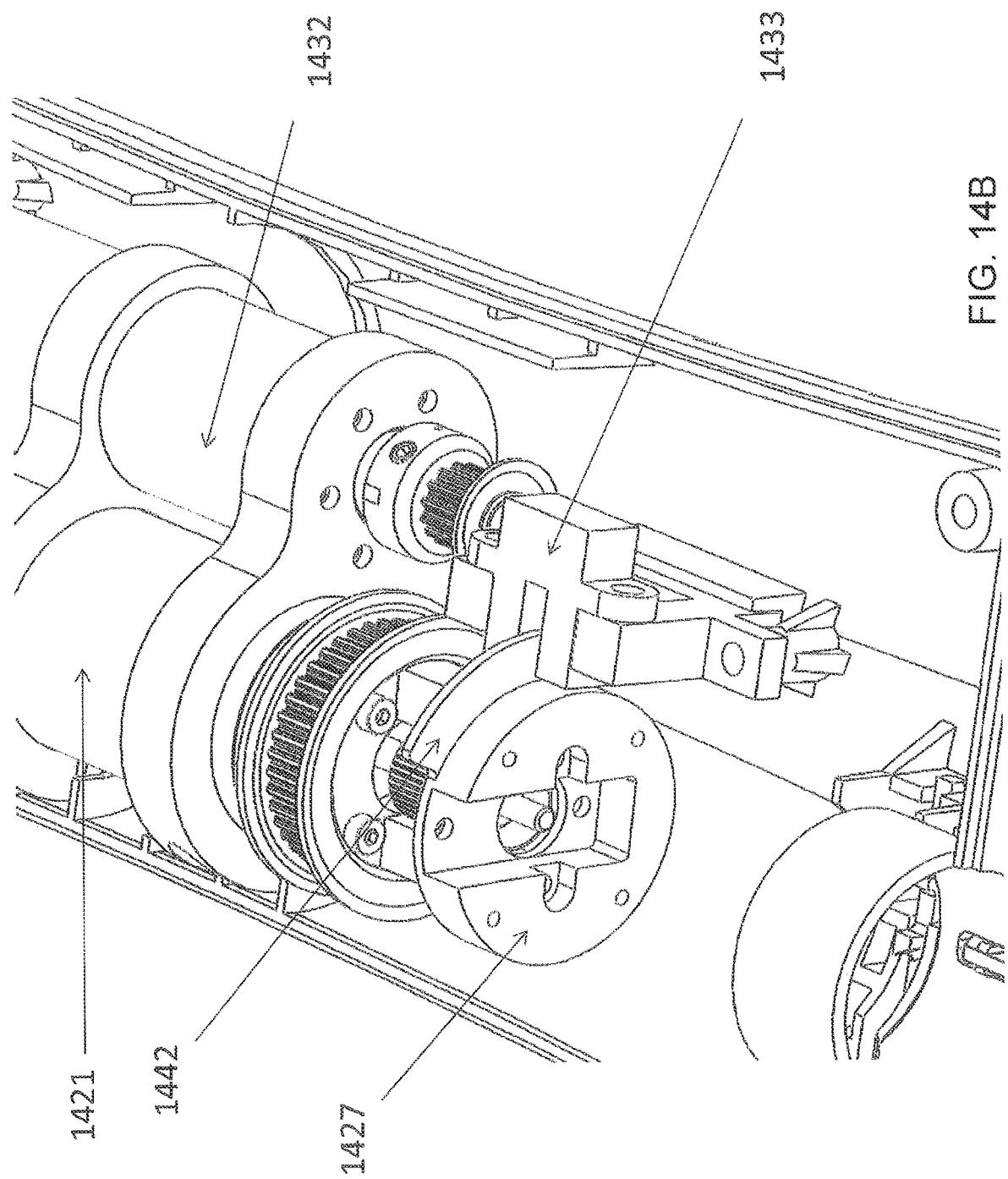

For example, referring to FIGS. 14A-14B, the drive assembly 1400 can be automatically aligned with the catheter handle through alignment mechanisms on both the drive assembly 1400 and on the catheter handle. Thus, in one embodiment, the drive assembly 1400 can include an orientation sensor 1433 configured to sense the rotational position of the optical connector 1427. For example, as shown in FIGS. 14A-14B, the sensor 1433 can be a slot sensor (or optical fork sensor) configured to detect a flag 1442 on the optical connector 1427. The sensor 1433 (in this case, a slot sensor) can thus detect as the flag 1442 passes therethrough. Because the flag 1442 is in a set position relative to the connection mechanisms of the optical connector 1427, the detection of the flag 1442 can allow for the determination of the rotational position or orientation of the connection mechanisms.

Figure 15:
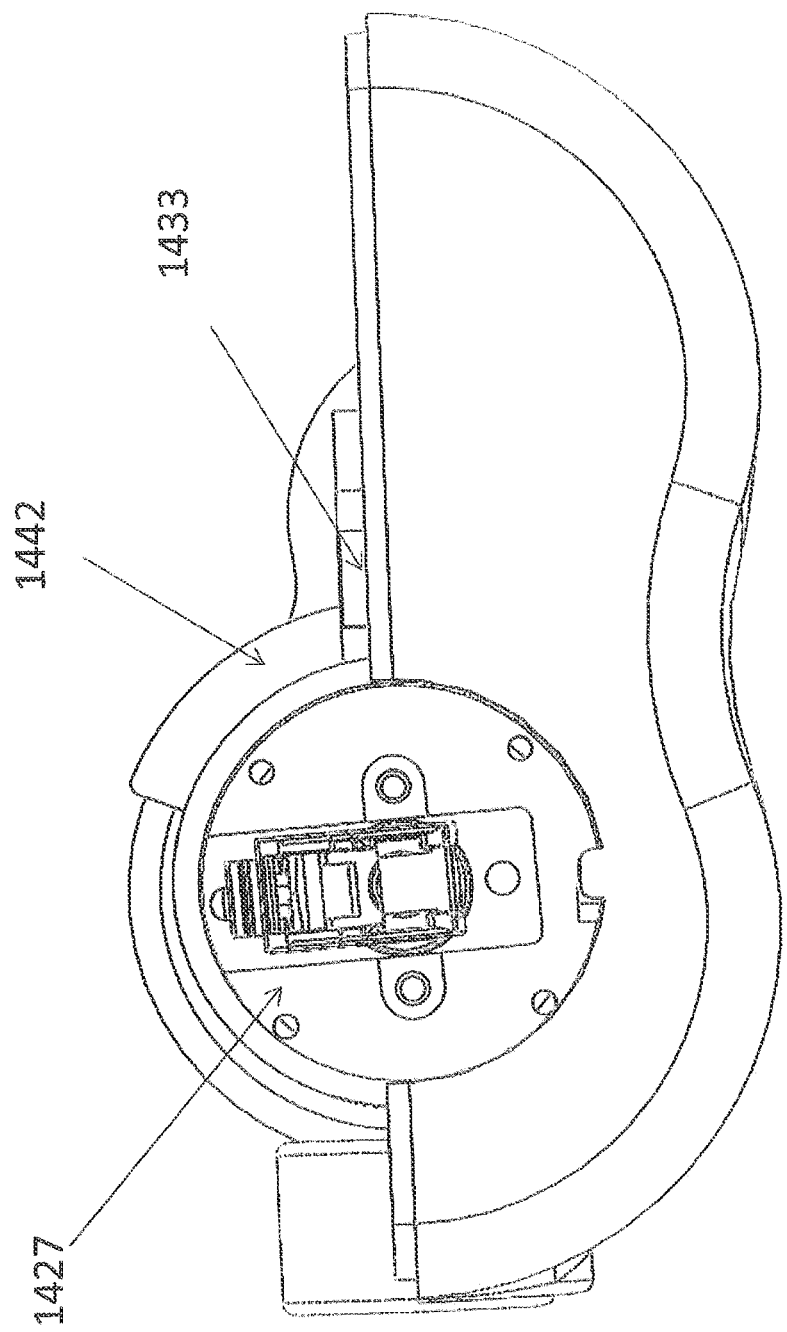
FIG. 15 shows an axial view of a handle lock of the drive assembly of FIGS. 7 and 8 with the optical connector aligned in top-dead-center position.

When the user powers the drive assembly 1400 off, a control board in the drive assembly 1400 can use feedback from the optical sensor 1433 to stop the motor 1432 such that the optical connector 1427 is always in the same position, such as the top-dead center position shown in FIG. 15. That is, after the user powers the drive assembly 1400 off, the control board can keep the motor 1432 and FORJ 1421 running at a constant speed until the exact position of the optical connector 1427 is identified based upon readings from the sensor 1433. The control board can then cut power to the motor such that, based upon the sensed position and the known length of time that the FORJ takes to stop after power is cut, the optical connector 1427 will stop in a predetermined position. The predetermine position can be the same every time that the drive assembly 1400 is used.

Advantageously, if the optical connector 1427 always stops in the same position, it can mate with a handle or catheter that is preset in a corresponding mating optical position (such as set by the manufacturer). Such a feature can provide for an automatic optical connection when the drive assembly is physically attached to the catheter or handle in a set orientation, such as with the locking mechanism described above. In some embodiments, the physical relationship between the drive assembly 1400 and the handle or catheter can be set, such as with a mating tooth (e.g. a protruding tooth or rib on the drive assembly and a recessed slot on the catheter handle).

Advantageously, the drive assembly 1400 can be less than 3 lbs, such as less than 2 lbs, such as approximately 1.5 lbs in weight. Further, the drive assembly can be less than 90 cubic inches, such as less than 75 cubic inches, such as less than 65 cubic inches, for example approximately 63 cubic inches in volume. In one embodiment, the drive assembly 1400 can measure 9" by 3.5" by 2".

Figure 17:
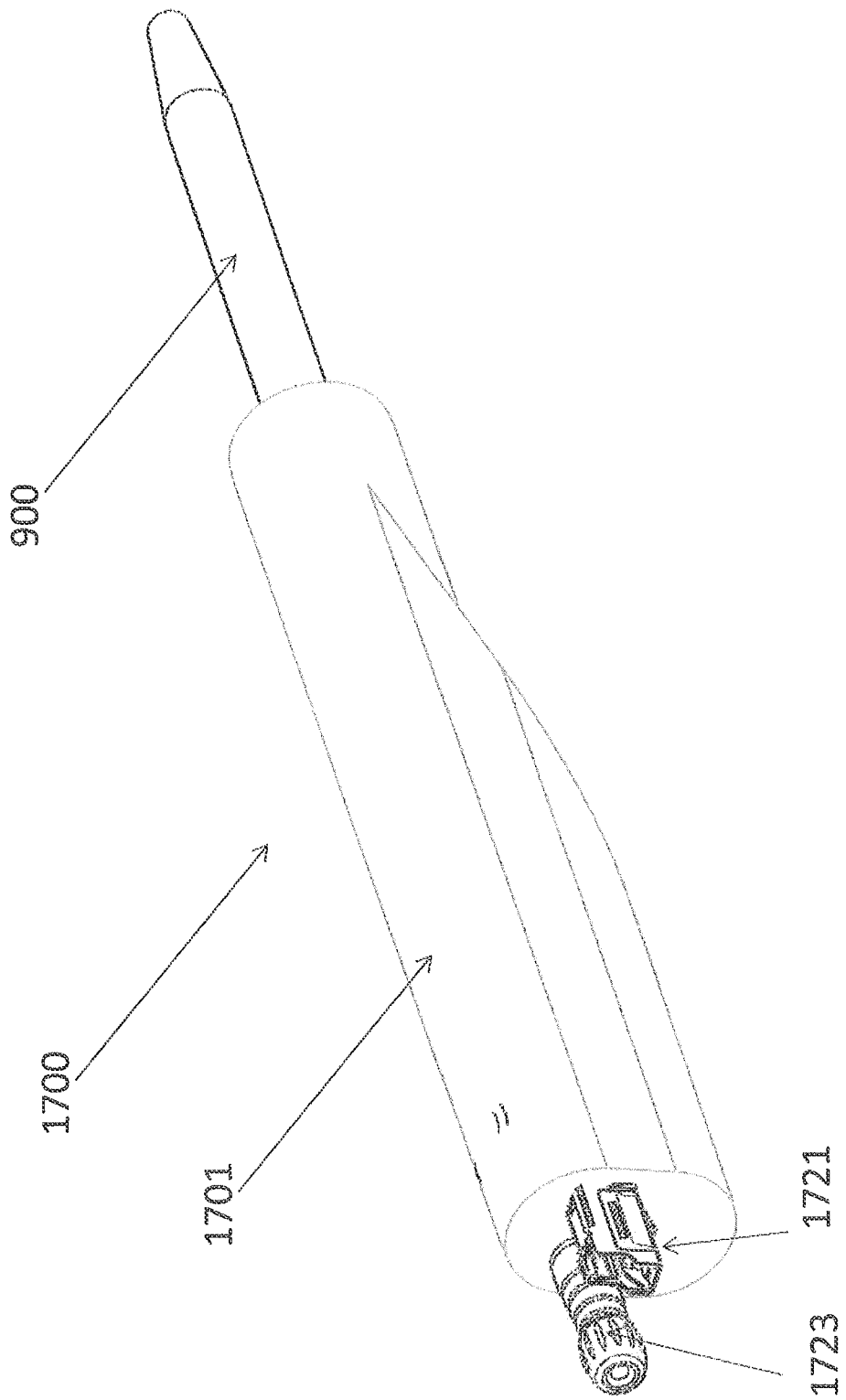
FIG. 17 shows another exemplary drive assembly.
Figure 18A:
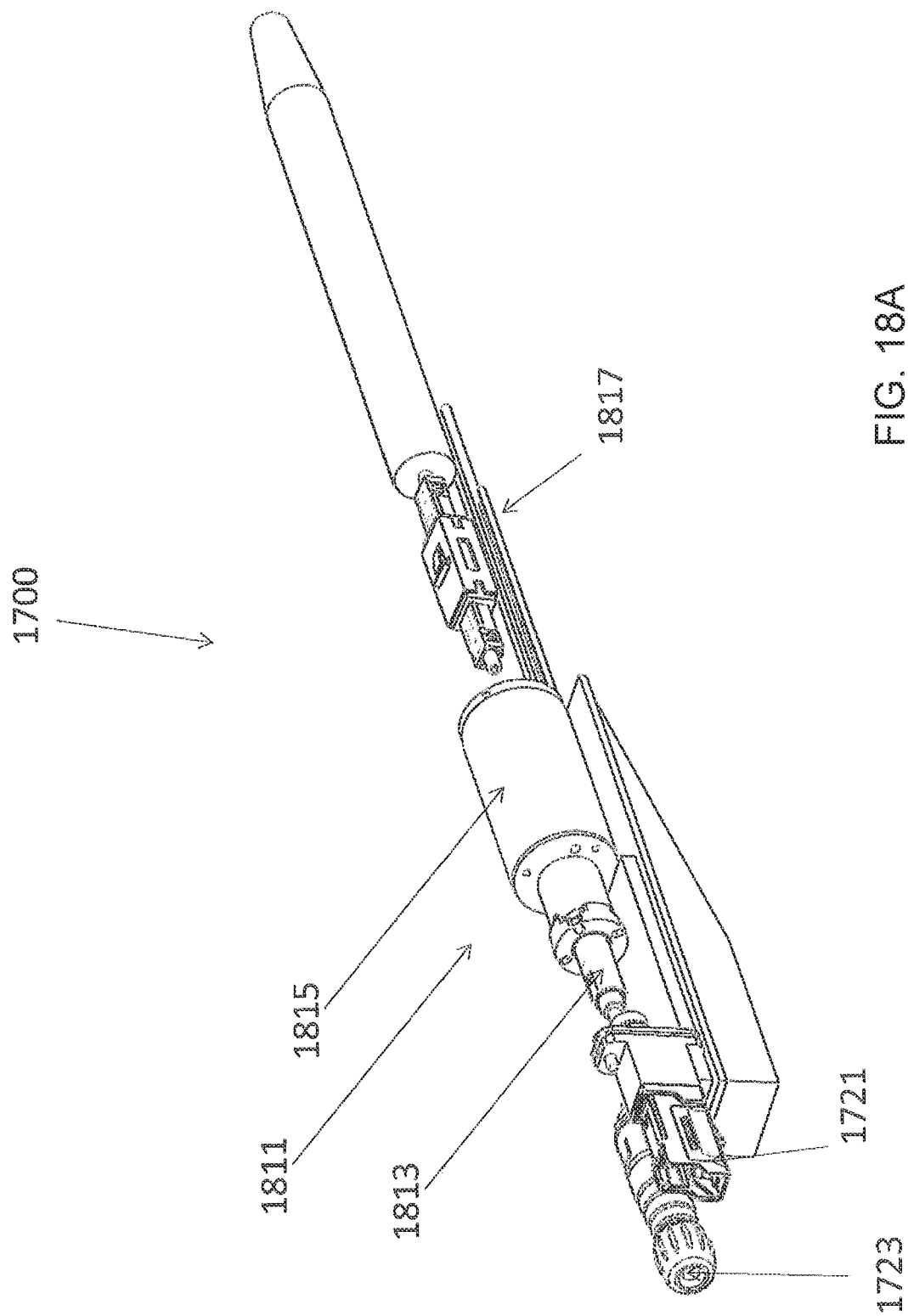
FIGS. 18A-18C show the drive assembly of FIG. 17 with the housing removed.
Figure 18B:
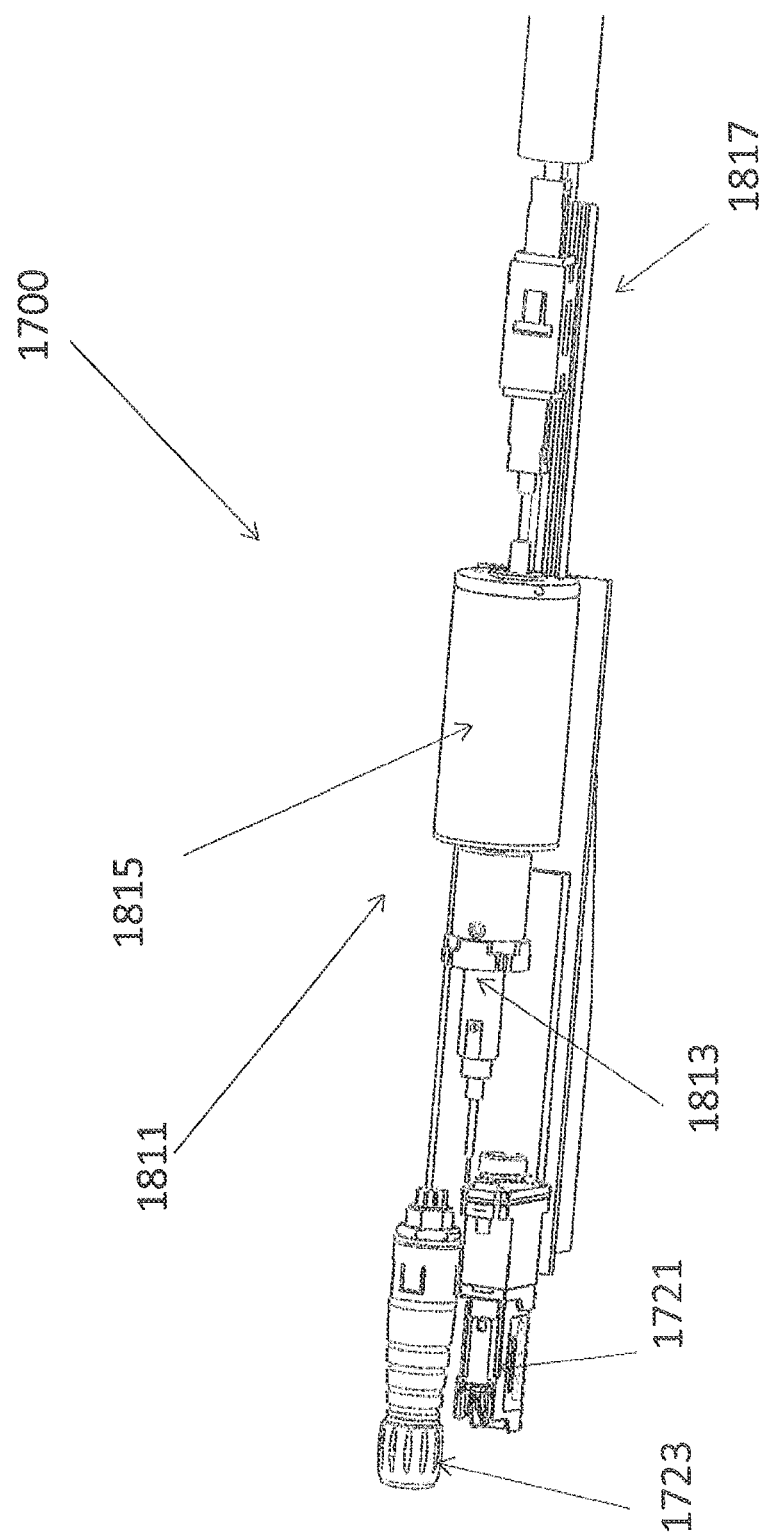
Figure 18C:
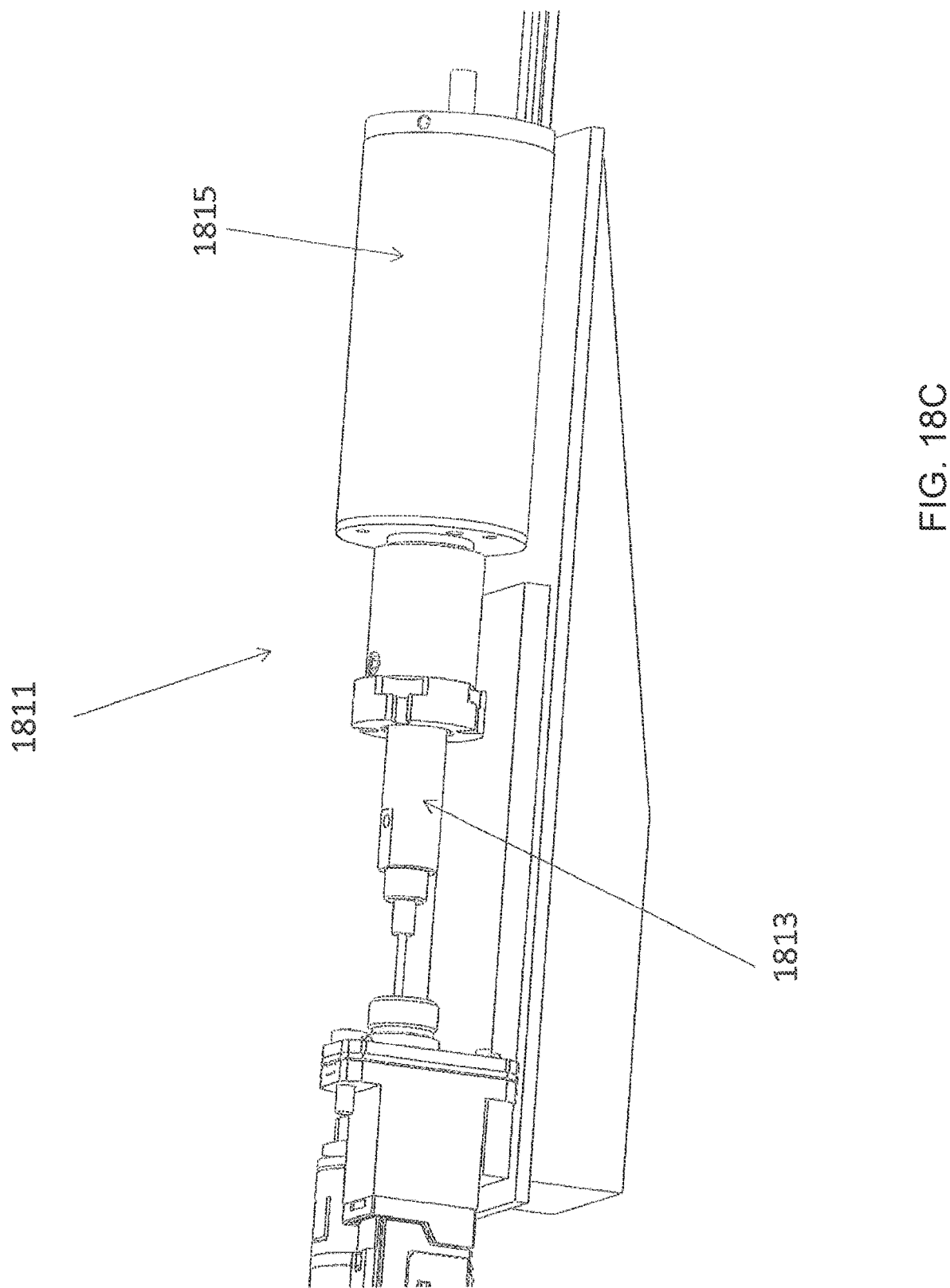
Figure 19:
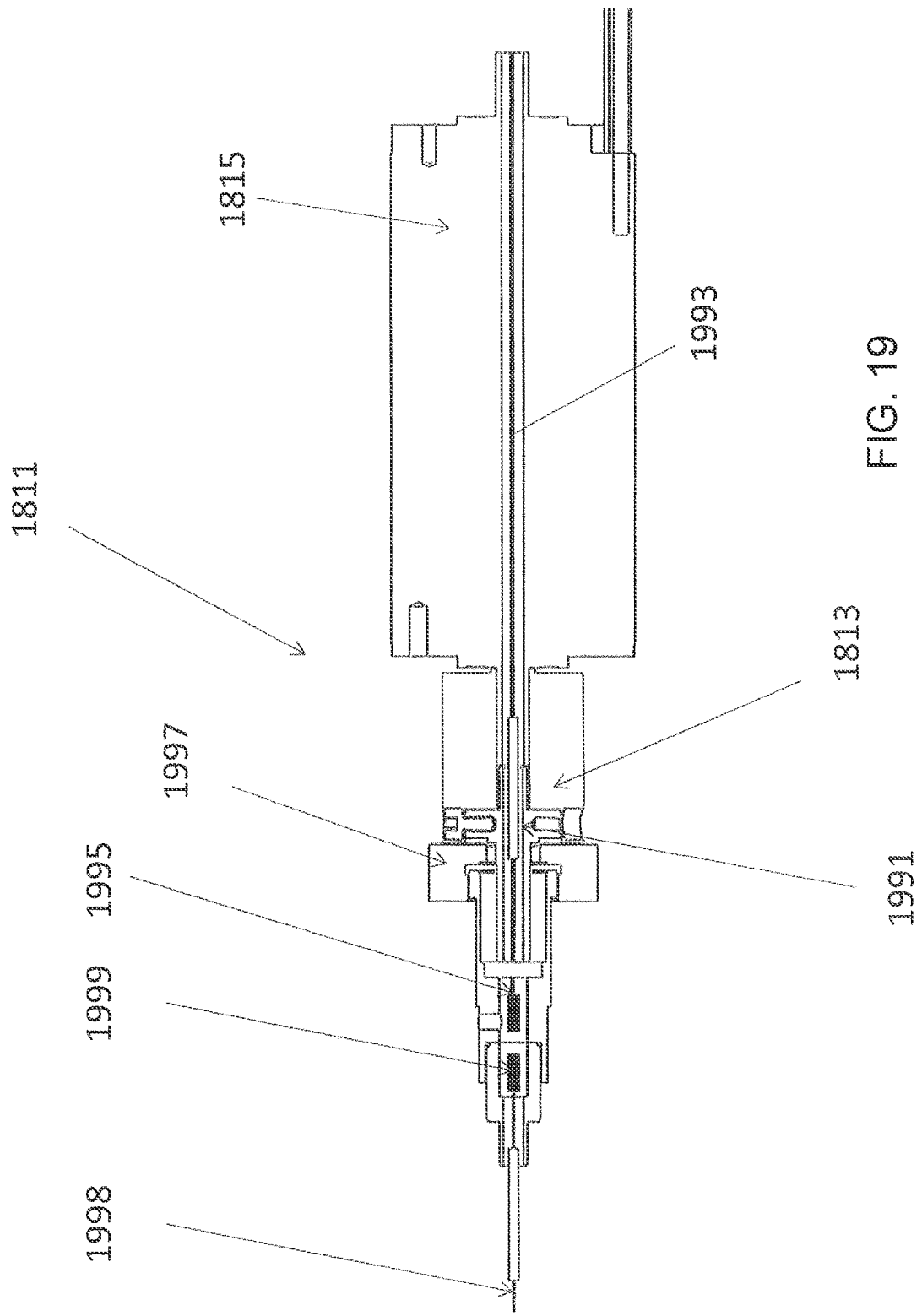
FIG. 19 is a cross-sectional diagrammatic view of the rotary optical drive subassembly of FIGS. 18A-18C.

Another drive assembly 1700 is shown with respect to FIGS. 17-19 that can be configured to provide rotation of a drive shaft and rotation of an optical fiber of an imaging catheter.

Referring to FIG. 17, the drive assembly 1700 can include a housing 1701, an optical connector 1721 configured to connect the drive assembly 1700 to a light source, a power connector 1723 configured to connect the drive assembly 1700 to a power source, and a connection 1755 (such as the handle locks described above) configured to connect the drive assembly 1700 to a handle 900 of an imaging catheter.

As shown in FIG. 18A-19 the drive assembly 1700 can include a rotating optical drive subassembly 1811 including a FORJ 1813, a motor 1815, and an optical connector 1817, such as an MU adaptor, configured to connect the FORJ with the catheter drive shaft and optical fiber. The shaft of the motor 1815 can be hollow so as to allow the FORJ 1813 to extend therethrough (i.e., the motor 1815 and the FORJ 1813 can be coaxial). In one embodiment, as shown in FIG. 19, the FORJ 1813 is entirely on the stationary side of the motor, with only a rotating fiber 1993 passing through the motor 1815. In another embodiment, the FORJ 1813 works through the motor 1815, with a stationary fiber on one side, light passing through the hollow shaft, and a rotating fiber on the far side. In yet another embodiment, the FORJ 1813 is on the rotating side of the motor 1815 and a stationary fiber inside a stationary tube passes through the motor 1815. The motor 1815 can further be configured to provide sufficient torque without gearing. Further, the connector 1817 can be configured to as to minimize the moment of inertia and swept volume to reduce vibration.

Advantageously, by having the motor 1815 and the FORJ 1813 coaxial, the dimensions of the drive assembly 1700 can be reduced. For example, the drive assembly 1700 can have a volume of less than 40 cubic inches, such as less than 20 cubic inches, such as less than 18 cubic inches, such as approximately 14-16 cubic inches. Further, the drive assembly 1700 can have a length of less than or equal to nine inches and a diameter of less than or equal to 2.5 inches, such as approximately 1.25 inches. In exemplary embodiments, the drive assembly 1700 is approximately 9" long by 1.5" in diameter, 9" long by 1.25" in diameter, or 7" long by 1.25" in diameter.

Like the other drive assemblies described herein, when motor 1815 rotates, the FORJ 1813 can rotate, thereby causing the optical connector 1817 (and thus the drive shaft and optical fiber of the imaging catheter) to rotate. Further, similar to the drive assembly 1400, the drive assembly 1700 can include a mechanism for automatically/mechanically aligning the drive assembly 1700 with the handle or catheter, such as a top dead center sensor.

Referring to FIG. 19, it is to be understood that the FORJ 1815 (and any FORJ described herein) can include a rotating portion 1991 with a rotating fiber 1993 and a rotating lens 1995 and a stationary portion 1997 with a stationary fiber 1998 and a stationary lens 1999.

Figure 16:
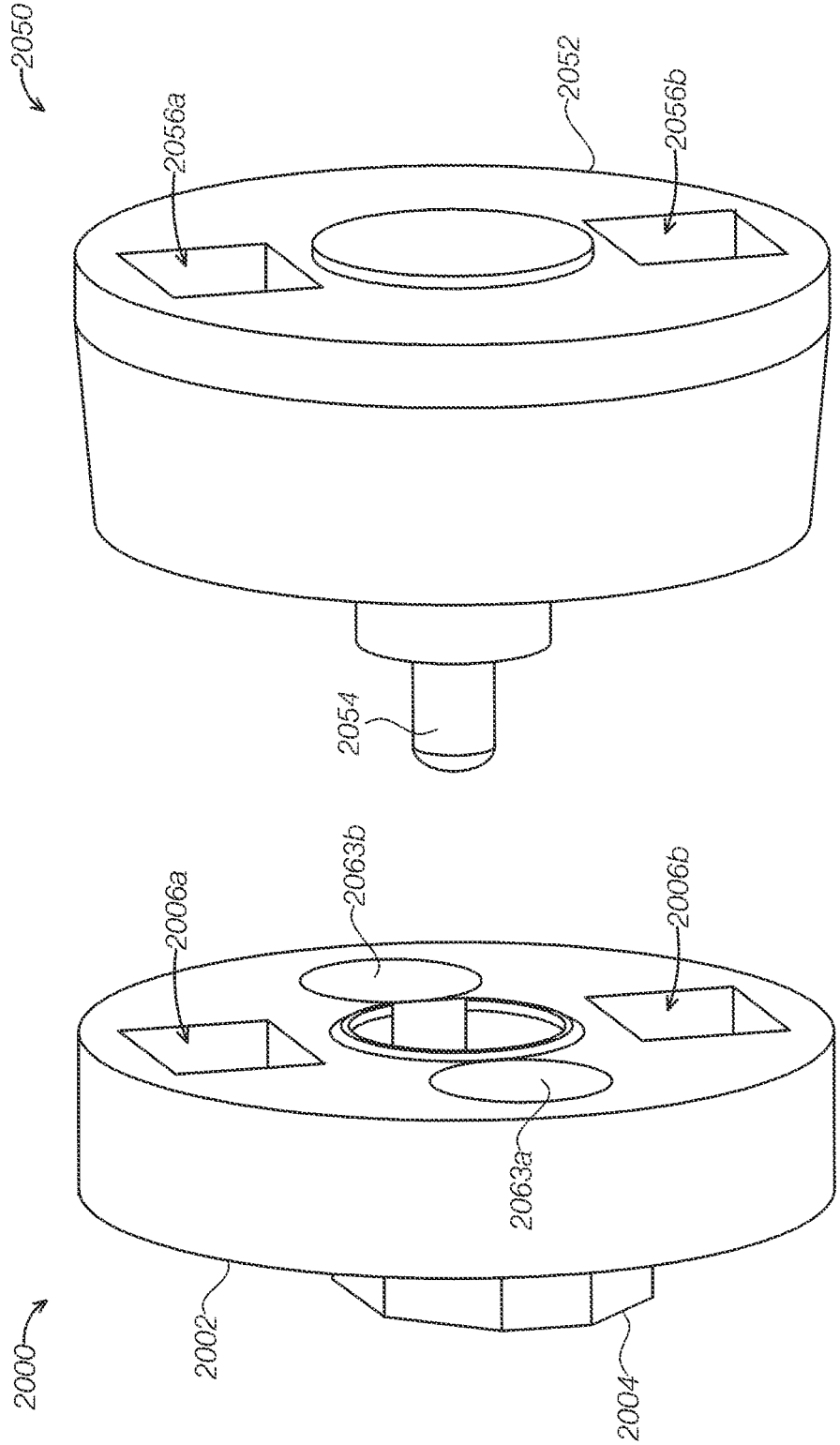
FIG. 16 shows a magnetic connector for connecting a catheter to a drive assembly.

Referring to FIG. 16, in some embodiments, the drive assemblies described herein can include a magnetic handle locking assembly 2000 in place of the locking mechanisms described above. The locking assembly 2000 can be configured to mate with a magnetic assembly 2050 on the catheter handle.

In one embodiment, shown in FIG. 16, the locking assembly 2000 can include a magnetic housing 2002 and a female fiber optic connector 2004, such as an FC-APCC, which can be configured to mate with a catheter magnetic housing 2052 and a male fiber optic connector 2054, such as an FC-APC 2054 (though in other embodiments, the positions of the female/male FC-APCs could be reversed). The housings 2002, 2052 can include slots 2006*a,b* and 2056*a,b* configured to hold magnets therein. The magnets in each slot 2006*a,b* of the drive assembly can be of opposite polarity to one another. Further, the magnets in slots 2006*a,b* can be of opposite polarity to the magnets in the adjacent catheter locking assembly (e.g., magnets in slot 2006*a* can be of opposite polarity to magnets in slot 2056*a*). Thus, if the magnetic assemblies 2000, 2050 are not properly aligned, the opposing polarities of the magnets can cause the assemblies 2000, 2050 to rotate into the proper alignment, thus providing an automatic alignment feature for the drive assemblies described herein with a corresponding imaging catheter handle.

The locking assembly 2000 can further include mechanical teeth and mating slots 2063*a,b* therein configured to hold the magnetic assemblies 2000, 2050 together as one or the other is rotated, thereby transmitting torque from one assembly 2000 to the other 2050.

Advantageously, the magnetic handle locking assembly 2000 can allow insertion of the catheter into the drive assembly with a single hand without requiring a secondary fiber connection, in contrast to other drive assemblies where the optical connection was manually made after the mechanical connection was made.

The drive assemblies described herein can be reusable, advantageously reducing the cost and complexity associated with imaging catheters.

Further, the drive assemblies described herein can advantageously be introduced into the sterile field through use of a sterile bag. For example, a non-sterile operator, using sterile technique, can open the sterile bag pouch and present the sterile bag to the sterile operator. The sterile operator can remove the bag from the sterile pouch and pass the catheter handle through the sterile bag. The non-sterile operator can then present the drive assembly 100 to the sterile operator. The sterile operator can connect the catheter handle into the handle lock until the catheter is locked into place. The non-sterile operator can connect the optical connector 446 to the catheter and close the access door 107 of housing 101. The non-sterile operator can further grab the outside of the bag and pull the bag back over the drive assembly and attached cables. Finally, the sterile operator can position the bagged drive assembly in the sterile field where desired. The drive assembly can be activated through toggling of the power switch. Similar methodologies can be used with the drive assemblies 1400 and 1700 described herein, though the automatic optical connection between the drive assemblies 1400 and 1700 advantageously eliminates the step of creating a separate optical connection (such as by opening the access door 107 of the drive assembly 100).

It is to be understood that any of the features of the various exemplary drive assemblies described herein could be substituted or added to other drive assemblies while still lying within the scope of this disclosure.

The drive assemblies described herein can be used to transmit light from a source, such as for optical coherence tomography. Exemplary imaging systems that can be used with the drive assemblies are described in copending Patent Applications: U.S. patent application Ser. No. 12/790,703, titled "OPTICAL COHERENCE TOMOGRAPHY FOR BIOLOGICAL IMAGING," filed May 28, 2010, Publication No. US-2010-0305452-A1; U.S. patent application Ser. No. 12/829,267, titled "CATHETER-BASED OFF-AXIS OPTICAL COHERENCE TOMOGRAPHY IMAGING SYSTEM," filed Jul. 1, 2010, Publication No. US-2010-0021926-A1; and International Patent Application No. PCT/US2013/031951 titled "OPTICAL COHERENCE TOMOGRAPHY WITH GRADED INDEX FIBER FOR BIOLOGICAL IMAGING," all of which are incorporated by reference in their entireties.

The drive assemblies described herein can be used with a variety of different catheters, such as atherectomy catheters with imaging. Exemplary catheters and/or handles that can be used with the drive assemblies described herein are set forth in U.S. Patent Applications: U.S. patent application Ser. No. 12/829,277, titled "ATHERECTOMY CATHETER WITH LATERALLY-DISPLACEABLE TIP," filed Jul. 1, 2010, Publication No. US-2011-0004107-A1; U.S. patent application Ser. No. 13/175,232, titled "ATHERECTOMY CATHETERS WITH LONGITUDINALLY DISPLACEABLE DRIVE SHAFTS," filed Jul. 1, 2011, Publication No. US-2012-0046679-A1; U.S. patent application Ser. No. 13/654,357, titled "ATHERECTOMY CATHETERS AND NON-CONTACT ACTUATION MECHANISM FOR CATHETERS," filed Oct. 17, 2012; U.S. patent application Ser. No. 13/675,867, titled "OCCLUSION-CROSSING DEVICES, ATHERECTOMY DEVICES, AND IMAGING," filed Nov. 13, 2012; International Patent Application No. PCT/US2013/031901 titled "ATHERECTOMY CATHETERS WITH IMAGING," filed Mar. 15, 2013; and International Patent Application No. PCT/US2013/032494 titled "BALLOON ATHERECTOMY CATHETERS WITH IMAGING," filed Mar. 15, 2013, all of which are incorporated by reference in their entireties.

Additional details pertinent to the present invention, including materials and manufacturing techniques, may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. A drive assembly for driving an imaging catheter having a rotatable fiber and a rotatable drive shaft, the drive assembly comprising:
   a drive assembly housing;
   a rotary optical subassembly within the housing and comprising a fiber optic rotating junction having a stationary portion with a stationary fiber therein and a rotatable portion with a rotatable fiber therein; and
   a linear slide within the housing, wherein the rotary optical subassembly rests on a translatable portion of the linear slide, the linear slide configured to translate the fiber optic rotating junction axially within the housing.

2. The drive assembly of claim 1, wherein the linear slide comprises a stationary portion connected to the housing.

3. The drive assembly of claim 1, wherein the translatable portion is movable relative to the housing.

4. The drive assembly of claim 1, further comprising a locking mechanism on the housing configured to either allow or restrict the rotary optical subassembly from translating.

5. The drive assembly of claim 1, further comprising a handle lock configured to secure a catheter handle of an imaging catheter assembly to the housing.

6. The drive assembly of claim 1, wherein the translatable portion of the linear slide is configured to translate relative to the housing and to a catheter outer shaft, when the handle lock is secured to a catheter handle of the imaging catheter.

7. The drive assembly of claim 1, wherein the stationary fiber of the fiber optic rotating junction includes slack configured to account for translation of the fiber optic rotating junction.

8. The drive assembly of claim 7, wherein the linear slide comprises a space configured to receive the fiber optic rotating junction slack.

9. The drive assembly of claim 1, wherein a volume of the drive assembly housing is less than 40 cubic inches, and wherein the drive assembly has a total weight of less than 2 pounds.

10. A drive assembly for driving an imaging catheter having a rotatable fiber and a rotatable drive shaft, the drive assembly comprising:
    a drive assembly housing;
    a fiber optic rotating junction within the housing, the fiber optic rotating junction having a stationary portion with a stationary fiber therein and a rotatable portion with a rotatable fiber therein; and
    a linear slide in the housing, the linear slide configured to translate the fiber optic rotating junction axially within the housing, wherein the housing is less than 75 cubic inches in volume, and wherein the drive assembly has a total weight of less than 2 pounds.

* * * * *